(12) United States Patent
Inamdar et al.

(10) Patent No.: US 11,712,262 B2
(45) Date of Patent: Aug. 1, 2023

(54) SURGICAL INSTRUMENT WITH SUCTION CONTROL

(71) Applicant: Covidien LP, Mansfield, MA (US)

(72) Inventors: Tejas Satish Inamdar, San Francisco, CA (US); Mireille Akilian, Candia, NH (US); Peter Cesarini, Londonderry, NH (US)

(73) Assignee: Covidien LP, Mansfield, MA (US)

( * ) Notice: Subject to any disclaimer, the term of this patent is extended or adjusted under 35 U.S.C. 154(b) by 331 days.

(21) Appl. No.: 17/069,170

(22) Filed: Oct. 13, 2020

(65) Prior Publication Data

US 2021/0022767 A1 Jan. 28, 2021

Related U.S. Application Data

(62) Division of application No. 15/580,185, filed as application No. PCT/US2016/037372 on Jun. 14, 2016, now Pat. No. 10,799,264.

(Continued)

(51) Int. Cl.
*A61B 17/3207* (2006.01)
*A61B 17/32* (2006.01)
(Continued)

(52) U.S. Cl.
CPC ............... *A61B 17/320758* (2013.01); *A61B 17/32002* (2013.01); *A61B 90/03* (2016.02);
(Continued)

(58) Field of Classification Search
CPC ...... A61B 17/320758; A61B 17/32002; A61B 17/32075; A61B 17/320783; A61B 17/320725; A61B 90/03
See application file for complete search history.

(56) References Cited

U.S. PATENT DOCUMENTS 1,585,934 A 5/1926 Muir
1,666,332 A 4/1928 Hirsch
(Continued)

FOREIGN PATENT DOCUMENTS

CN 101522123 A 9/2009
CN 102006829 A 4/2011
(Continued)

OTHER PUBLICATIONS

Communication Pursuant to Article 94(3) EPC issued in corresponding European Application No. 16 731 485.5 dated Oct. 27, 2021, 4 pages.
(Continued)

*Primary Examiner* — Tuan V Nguyen
(74) *Attorney, Agent, or Firm* — Carter, DeLuca & Farrell LLP

(57) ABSTRACT

A surgical device includes an outer member, an inner member, and at least one locking element. The inner member is at least partially supported within the outer member. The at least one locking element is configured in a first arrangement of the surgical device to lock the inner member in a first position and configured in a second arrangement of the surgical device to unlock the inner member from the first position. The at least one locking element is configured to change from the first arrangement to the second arrangement upon coupling the inner member in an operational arrangement to a hand piece.

12 Claims, 14 Drawing Sheets

Related U.S. Application Data

(60) Provisional application No. 62/181,565, filed on Jun. 18, 2015.

(51) Int. Cl.
*A61B 90/00* (2016.01)
*A61B 17/00* (2006.01)
*A61B 17/42* (2006.01)

(52) U.S. Cl.
CPC ..... *A61B 17/42* (2013.01); *A61B 2017/00398* (2013.01); *A61B 2017/00455* (2013.01); *A61B 2017/00469* (2013.01); *A61B 2017/00477* (2013.01); *A61B 2017/4216* (2013.01); *A61B 2217/005* (2013.01)

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | Mcgurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,971,034 A | 11/1990 | Doi et al. |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Frese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,586,973 A | 12/1996 | Lemaire et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |

(56) References Cited

U.S. PATENT DOCUMENTS

| | | |
|---|---|---|
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,879,365 A | 3/1999 | Whitfield |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,766,844 B2 | 8/2010 | Sjostrom |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,465,421 B2 | 6/2013 | Finkman et al. |
| 8,528,563 B2 | 9/2013 | Gruber |
| 8,574,253 B2 | 11/2013 | Gruber et al. |
| 8,647,349 B2 | 2/2014 | Gruber et al. |
| 8,663,264 B2 | 3/2014 | Cesarini et al. |
| 8,678,999 B2 | 3/2014 | Isaacson |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 | 8/2015 | Sullivan et al. |
| 9,125,550 B2 | 9/2015 | Shener-Irmakoglu et al. |
| 9,155,454 B2 | 10/2015 | Sahney et al. |
| 9,259,233 B2 | 2/2016 | Gruber et al. |
| 10,799,264 B2 | 10/2020 | Inamdar et al. |
| 2005/0240206 A1 | 10/2005 | Sjostrom |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |
| 2011/0034943 A1 | 2/2011 | Churchill et al. |
| 2011/0077674 A1 | 3/2011 | Sullivan et al. |
| 2011/0118544 A1 | 5/2011 | Adams et al. |
| 2011/0166419 A1 | 7/2011 | Reif et al. |
| 2012/0067352 A1 | 3/2012 | Gruber et al. |
| 2012/0078038 A1 | 3/2012 | Sahney et al. |
| 2012/0215245 A1 | 8/2012 | Palmer et al. |
| 2013/0131452 A1 | 5/2013 | Kuroda et al. |
| 2014/0003183 A1 | 1/2014 | Song |
| 2014/0088526 A1 | 3/2014 | Mark |

FOREIGN PATENT DOCUMENTS

| | | |
|---|---|---|
| CN | 103327914 A | 9/2013 |
| DE | 3206381 A1 | 9/1983 |
| DE | 3339322 A1 | 5/1984 |
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |

(56) References Cited

FOREIGN PATENT DOCUMENTS

| | | |
|---|---|---|
| DE | 19751632 C1 | 9/1999 |
| DE | 19859217 A1 | 7/2000 |
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1623677 A1 | 2/2006 |
| EP | 1681022 A1 | 7/2006 |
| GB | 2093353 A | 9/1982 |
| GB | 2311468 A | 10/1997 |
| JP | 2001075416 A | 3/2001 |
| JP | 2002529185 A | 9/2002 |
| JP | 2002538889 A | 11/2002 |
| JP | 2003245247 A | 9/2003 |
| NL | 1006944 C2 | 3/1999 |
| WO | 8101648 A1 | 6/1981 |
| WO | 9211816 A2 | 7/1992 |
| WO | 9307821 A1 | 4/1993 |
| WO | 9315664 A1 | 8/1993 |
| WO | 9426181 A1 | 11/1994 |
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9810707 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 9012010 A1 | 3/2000 |
| WO | 0028890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0135831 A1 | 5/2001 |
| WO | 0158368 A1 | 8/2001 |
| WO | 0195810 A2 | 12/2001 |
| WO | 02069808 A2 | 9/2002 |
| WO | 03022164 A1 | 3/2003 |
| WO | 03077767 A1 | 9/2003 |
| WO | 2004006788 A1 | 1/2004 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 2007044833 A2 | 4/2007 |
| WO | 2008021716 A2 | 2/2008 |
| WO | 2012044705 A1 | 4/2012 |

OTHER PUBLICATIONS

Australian Examination Report issued in corresponding Australian Application No. 2016277923 dated Feb. 20, 2020, 3 pages.
Australian Examination Report issued in corresponding Australian Application No. 2016277923 dated Dec. 10, 2020, 4 pages.
Chinese Office Action issued in corresponding Chinese Application No. 201680048040.0 dated Dec. 1, 2020, 11 pages.
European Examination Report issued in corresponding European Application No. 16 731 485.5 dated Jan. 26, 2021, 5 pages.

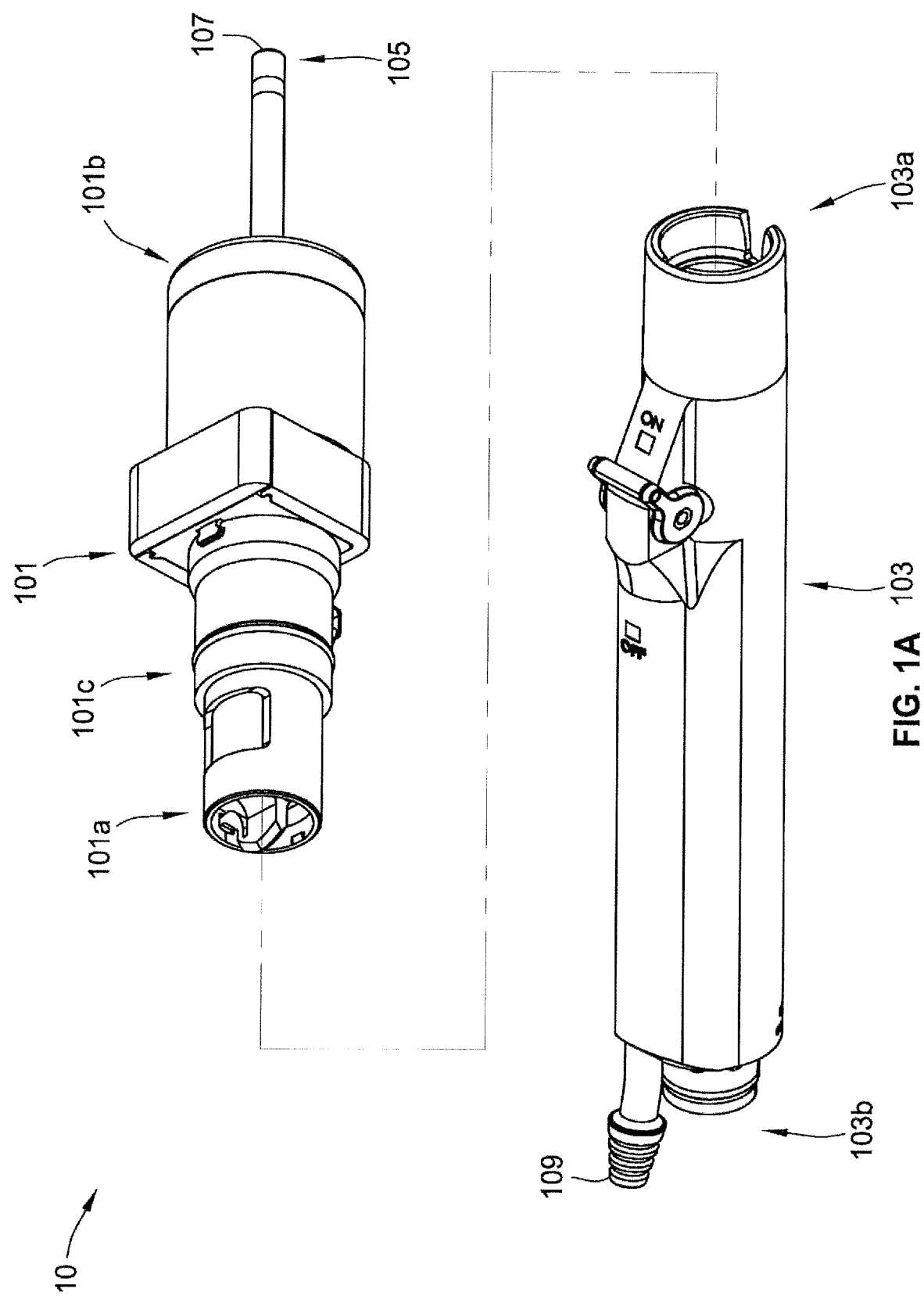

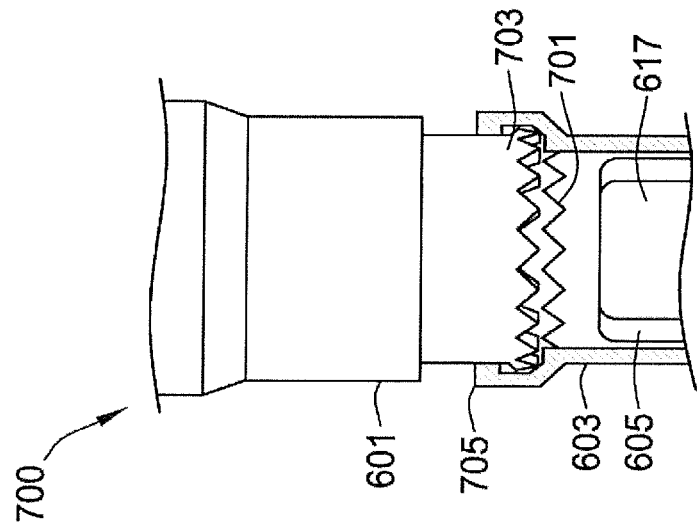
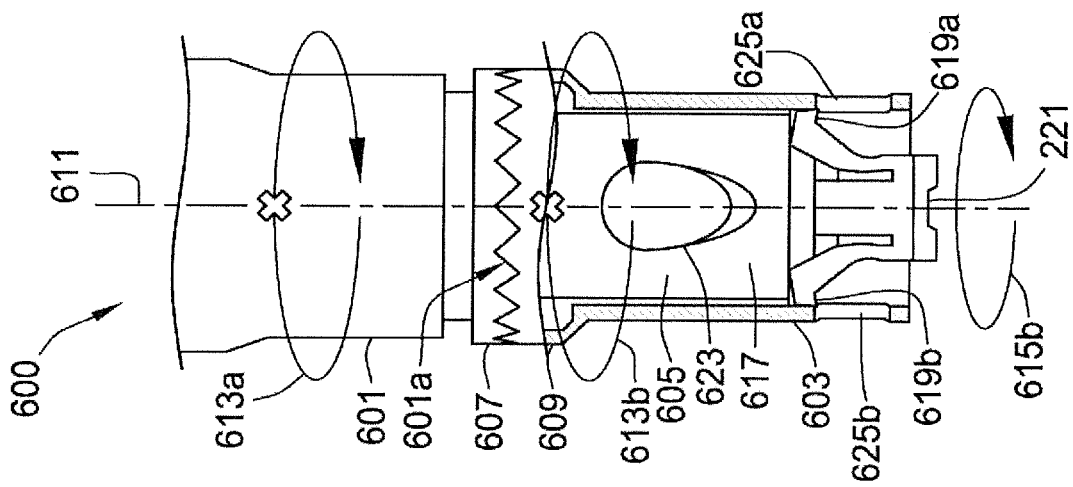
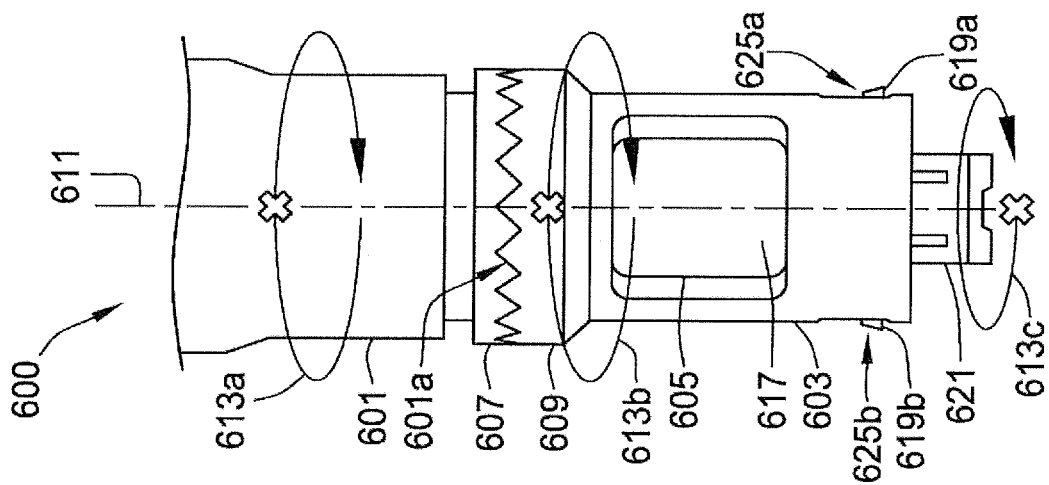

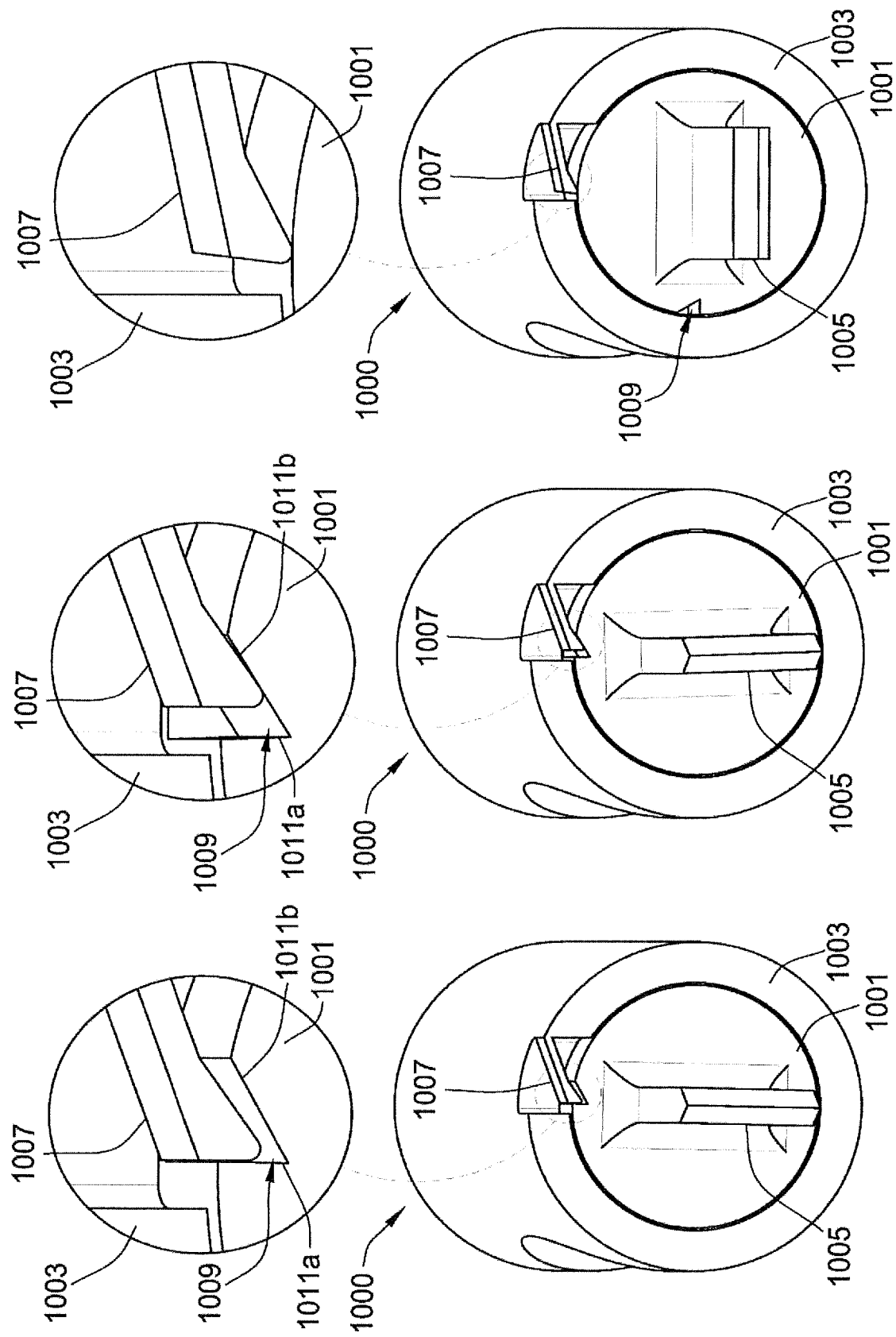

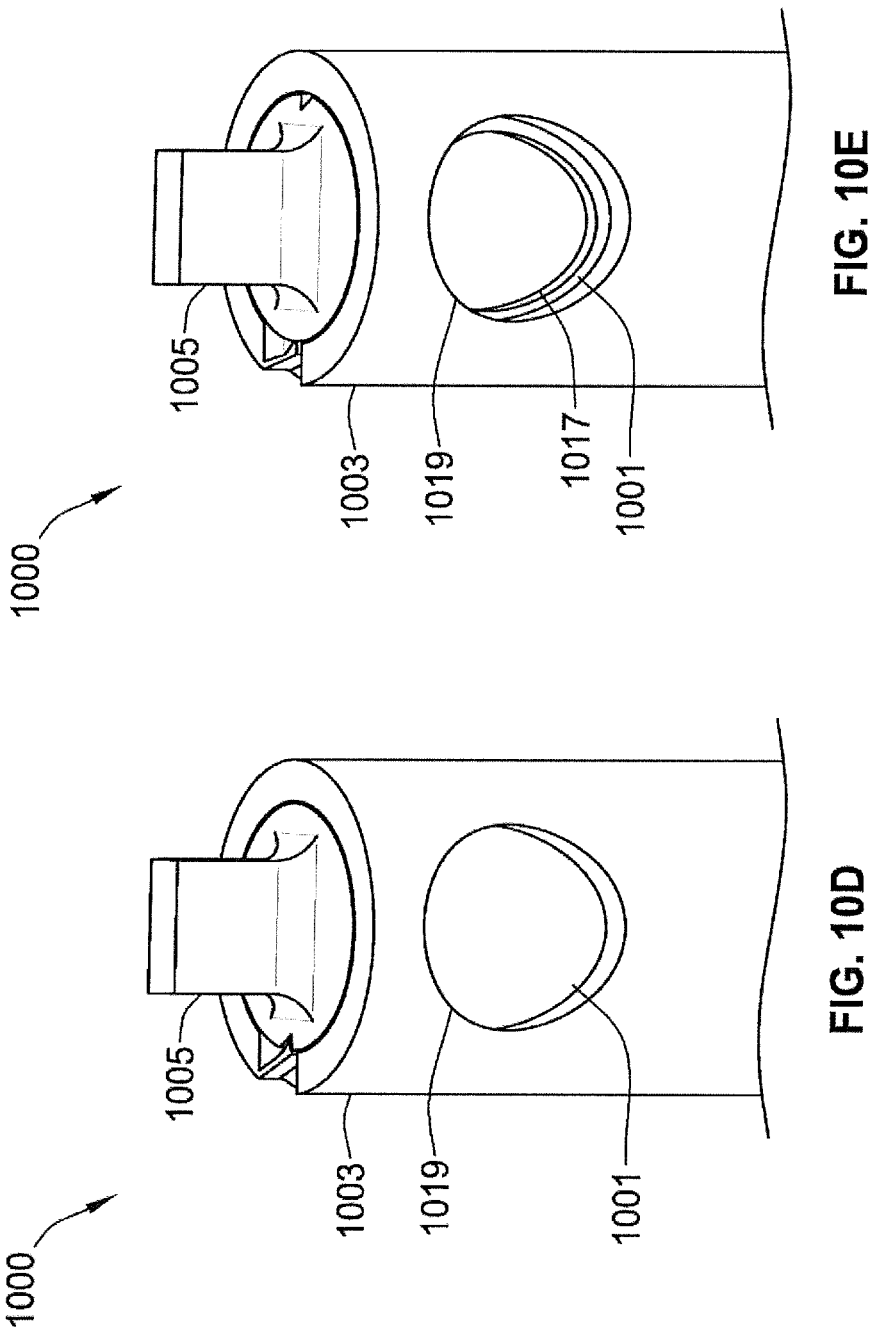

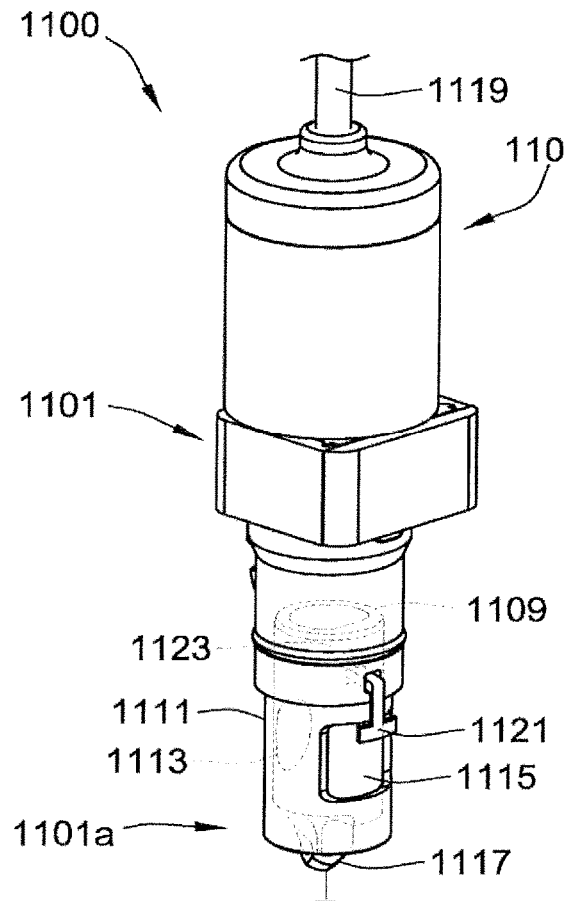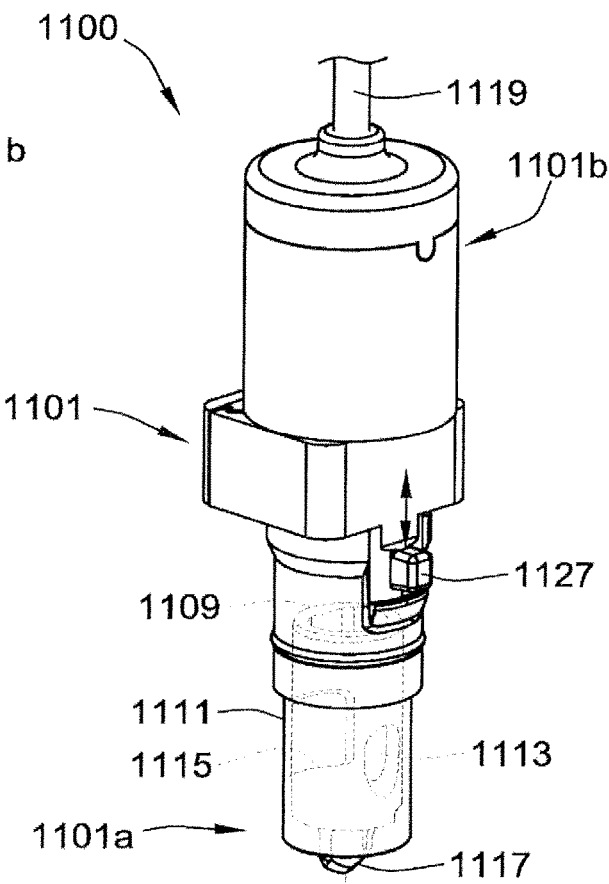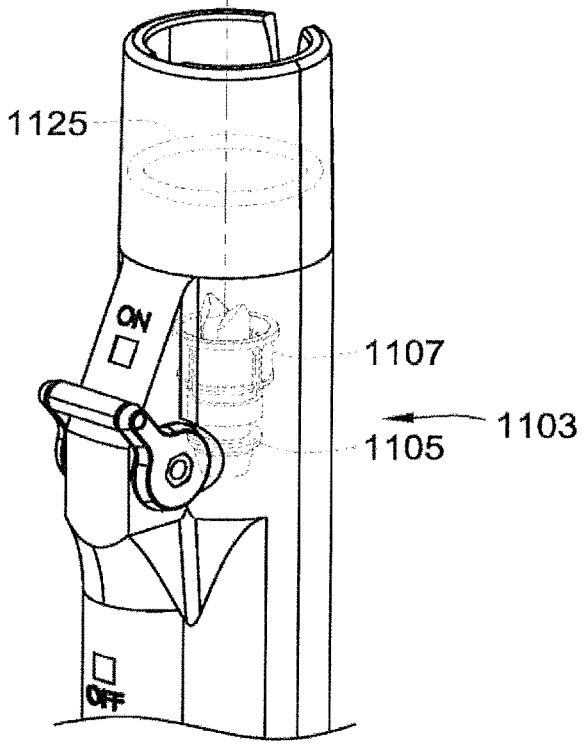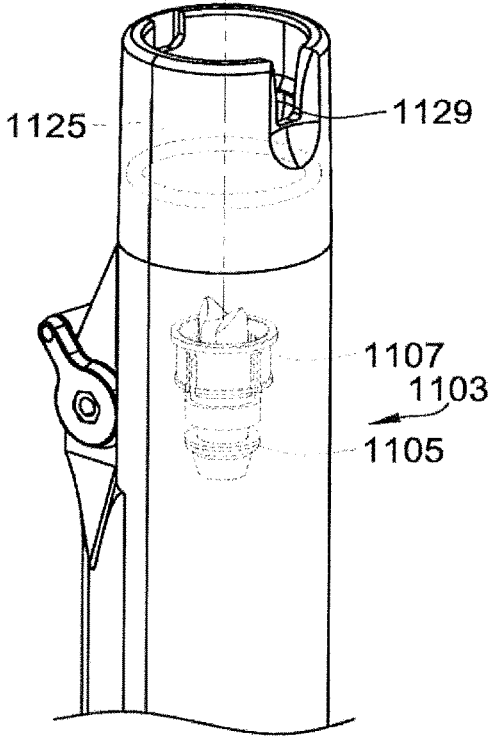
FIG. 11A  FIG. 11B

SURGICAL INSTRUMENT WITH SUCTION CONTROL

CROSS-REFERENCE TO RELATED APPLICATIONS

This application is a divisional application of U.S. patent application Ser. No. 15/580,185, filed on Dec. 6, 2017, now U.S. Pat. No. 10,799,264, which is a national stage application, under 35 U.S.C. § 371, of International Patent Application No. PCT/US2016/037372, filed on Jun. 14, 2016, which claims the benefit of and priority to U.S. Provisional Patent Application No. 62/181,565, filed on Jun. 18, 2015. The entire contents of each of the above-identified applications are hereby incorporated herein by reference.

BACKGROUND

Some surgical devices are adapted to aspirate fluid (or fluid and tissue) through a lumen in the surgical device. Endoscopic cutting systems include a cutting blade that can be removably coupled to a drive housing, and the drive housing can be removably coupled to a hand piece that includes a motor. The drive housing and the hand piece are configured to rotate and possibly translate the cutting blade. Some of the cutting blades include an outer tube having a cutting window wherein tissue drawn into the cutting window is resected and aspirated through the lumen of the cutting blade. The lumen is connected to a source of negative pressure (e.g., suction) that is used to aspirate tissue and distention or irrigation fluid. When the cutting window is open, the suction draws fluid (or fluid and tissue) out of the surgical site in order to maintain or improve visualization. While suction is desirable during cutting, it is not desirable when a user (e.g., a surgeon) is in the process of inserting the cutting blade into the endoscope at the beginning of the procedure, during the procedure when the user does not want suction, or when the user removes the cutting blade at the end of the procedure. In these instances, the motor is not energized and the cutting blade is not rotating.

If the cutting window or an outflow opening is open when then blade is inserted (or removed), the suction can cause uncontrolled fluid loss resulting in a loss of organ distention and increased turbulence, which reduces visualization. To avoid these problems, prior to inserting the cutting blade, a user must check (e.g., by visual inspection) and manually rotate the cutting blade to a window-closed position.

A need exists, therefore, for a locking mechanism in a surgical device that locks the drive housing in a suction-control position to provide suction control during insertion and/or removal of the surgical device, and when the surgical device is within the patient but not rotating (e.g., not cutting).

SUMMARY

According to some implementations of the present disclosure, a surgical device is disclosed that includes an outer member, an inner member, and at least one locking element. The inner member is at least partially supported within the outer member. The at least one locking element is configured in a first arrangement of the surgical device to lock the inner member in a first position and configured in a second arrangement of the surgical device to unlock the inner member from the first position. The at least one locking element is configured to change from the first arrangement to the second arrangement upon coupling the inner member in an operational arrangement to a hand piece.

According to additional implementations of the present disclosure, a surgical device is disclosed that includes an outer member and an inner member. The inner member is at least partially supported and moveable within the outer member. The surgical device further includes a flexible arm coupled to one of the outer member and the inner member. The surgical device also includes a recess within a surface of the other one of the outer member and the inner member. The recess is configured to accept the flexible arm. The recess and the flexible arm are configured to engage to resist rotational movement of the inner member relative to the outer member.

According to further implementations of the present disclosure, a surgical device is disclosed that includes an outer member, an inner member, and at least one locking element. The inner member is movable within the outer member. The at least one locking element is configured in a first arrangement to lock the inner member relative to the outer member and configured in a second arrangement to unlock the inner member relative to the outer member. Coupling the surgical device to a hand piece causes the at least one locking element to change from the first arrangement to the second arrangement.

The above summary is not intended to represent each implementation or every aspect of the present disclosure. Rather, the foregoing summary merely provides an exemplification of some of the novel implementations and features set forth herein. The above features and advantages, and other features and advantages of the present disclosure, will be readily apparent from the following detailed description of representative implementations and modes for carrying out the present implementations when taken in connection with the accompanying drawings and the appended claims.

BRIEF DESCRIPTION OF THE DRAWINGS

The disclosure will be better understood from the following description of exemplary implementations together with reference to the accompanying drawings, in which:

FIG. 1A is a perspective view of a surgical device that includes suction control, according to some implementations of the present disclosure;

FIGS. 6A-6D are top views of a drive housing, according to additional implementations of the present disclosure;

FIG. 7 is top view of a castellated region of a drive housing, according to some additional implementations of the present disclosure;

FIGS. 10A through 10C are end views of a drive housing, according to some additional implementations of the present disclosure;

FIGS. 10D and 10E are top views of the drive housing illustrated in FIGS. 10A through 10C, according to some additional implementations of the present disclosure;

FIGS. 11A and 11B are perspective views of a surgical device, according to some additional implementations of the present disclosure.

Figure 1B:
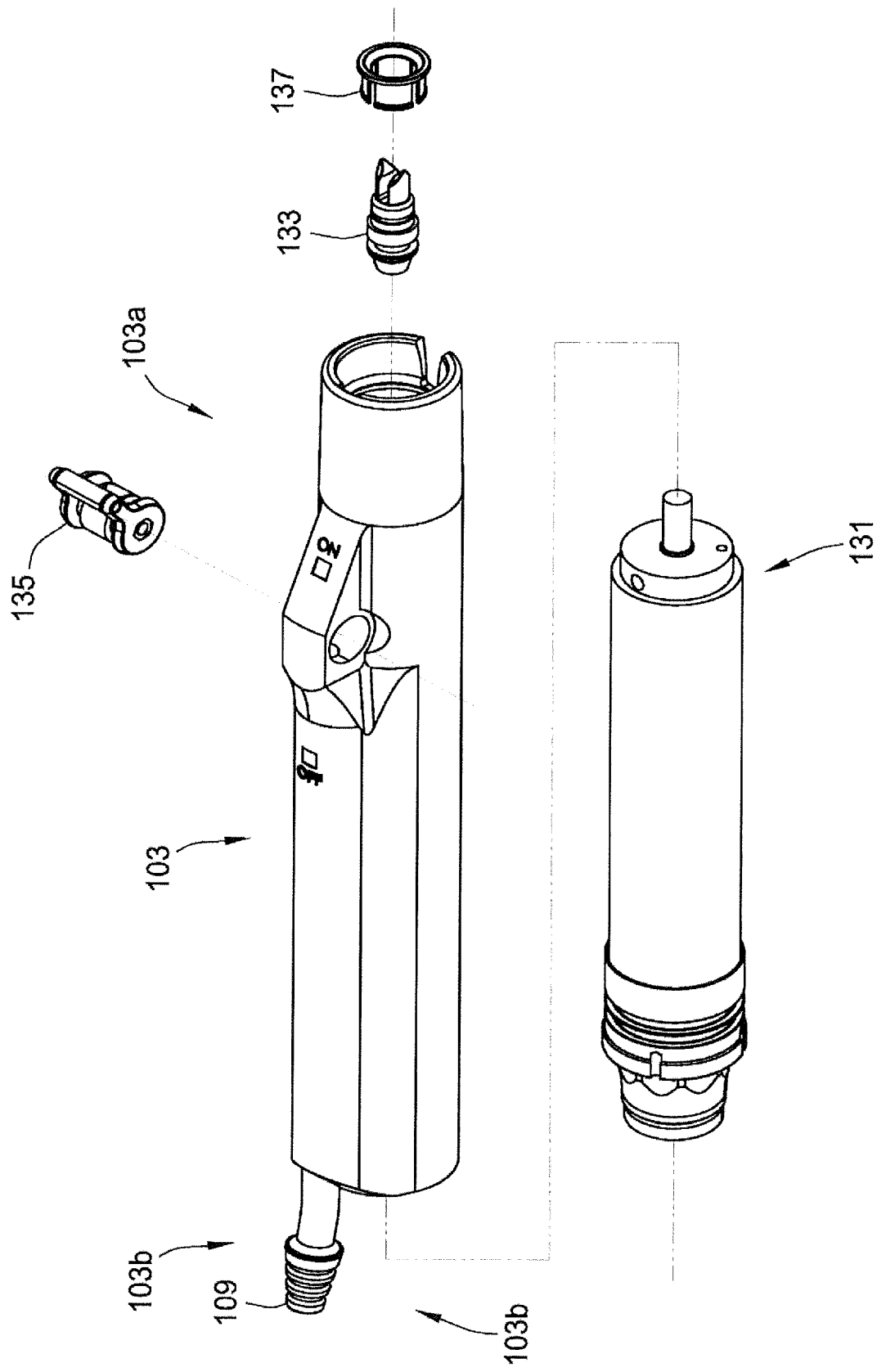
FIG. 1B is an exploded view of a hand piece of the surgical device of FIG. 1A, according to some implementations of the present disclosure.

While the disclosure is susceptible to various modifications and alternative forms, specific implementations thereof have been shown by way of example in the drawings and will be described in detail herein. It should be understood, however, that it is not intended to limit the disclosure to the particular forms disclosed, but on the contrary, the intention is to cover all modifications, equivalents, and alternatives falling within the spirit of the present disclosure.

DESCRIPTION

This disclosure is susceptible of implementation in many different forms. There are shown in the drawings, and will herein be described in detail, representative implementations with the understanding that the present disclosure is to be considered as an exemplification of the principles of the present disclosure and is not intended to limit the broad aspects of the disclosure to the implementations illustrated. To that extent, elements and features that are disclosed, for example, in the Abstract, Summary, and Detailed Description sections, but not explicitly set forth in the claims, should not be incorporated into the claims, singly or collectively, by implication, inference, or otherwise. For purposes of the present detailed description, unless specifically disclaimed: the singular includes the plural and vice versa; and the word "including" means "including without limitation."

According to the present disclosure, surgical devices are disclosed that include a suction-control position. Such a surgical device includes a drive housing that is in the suction-control position prior to being coupled to a hand piece. Accordingly, a user of the surgical device does not need to manually lock the window prior to inserting an insert portion (such as including a cutting blade) of the surgical device into a patient during a procedure. When the device is in the suction-control position, the suction can be controlled to resist fluid loss resulting in a loss of organ distention and to reduce or prevent increased turbulence to maintain visualization. Accordingly, prior to inserting the cutting blade, the user does not need to check by visual or other mode of inspection that the surgical device is in a window-closed position.

In an embodiment, the drive housing of such a surgical device includes an inner member that is in a suction-control position. In the suction-control position, the inner member's rotation is fixed, and the inner member cannot rotate relative to an outer member of the drive housing unless the drive housing is coupled to a hand piece. The fixed rotation of the inner member relative to the outer member ensures that the drive housing will be in the suction-control position upon coupling the drive housing to the hand piece, and can be in a suction-controlled (or closed) position upon inserting the device into a patient.

In alternate embodiments, by controlling when a motor of a hand piece that drives the drive housing stops and starts, a surgical device can ensure that, when the motor is stopped, the surgical device is in a suction-control position. Such control can be, for example, based on a counting of the number of rotations and only stopping the motor after a predefined number of rotations, or on a sensor in the hand piece. Accordingly, uncontrolled fluid loss and/or turbulence can be controlled at the start and stop of a procedure using the surgical devices disclosed herein.

Figure 1C:
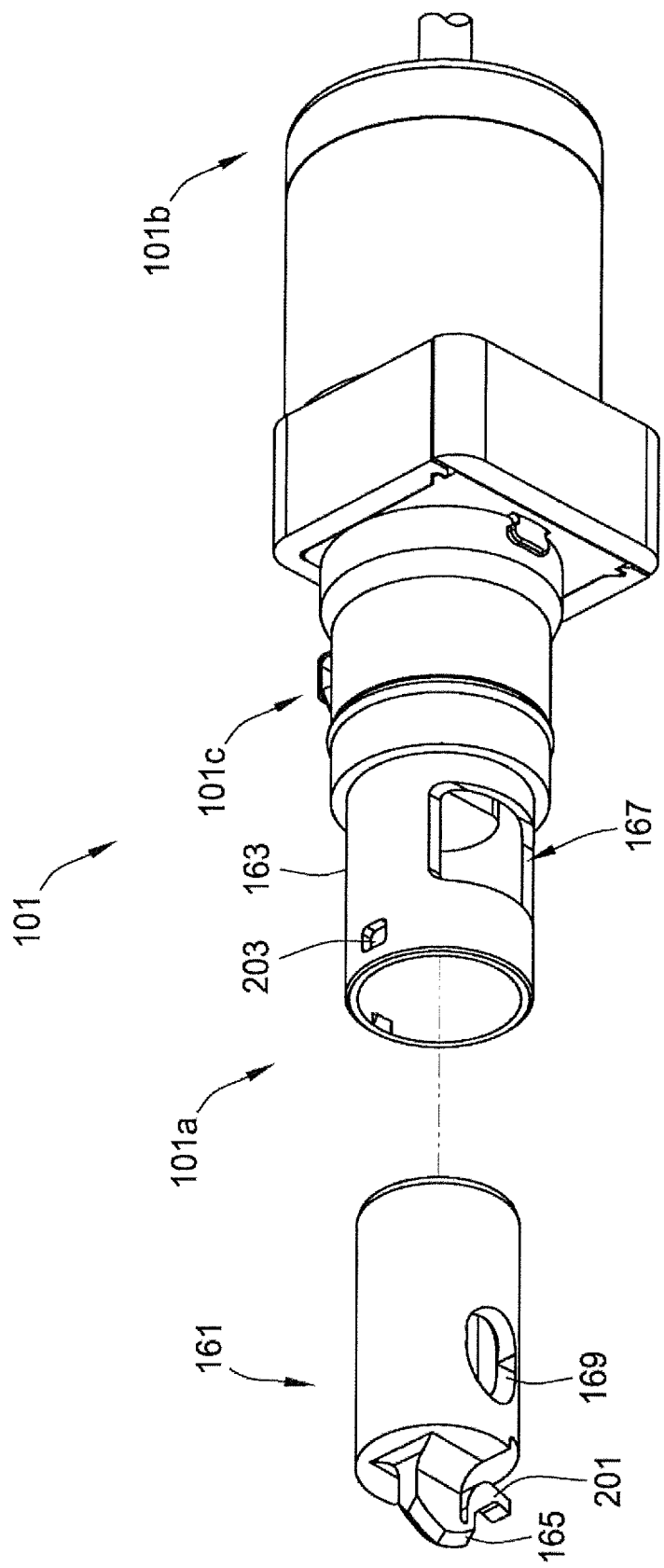
FIG. 1C is an exploded view of a drive housing of the surgical device of FIG. 1A, according to some implementations of the present disclosure.

Referring to FIGS. 1A-1C, FIG. 1A is a perspective view of an embodiment of a surgical device 10 that includes a suction-control configuration, according to some implementations of the present disclosure. The surgical device 10 includes a drive housing 101 and a hand piece 103. A proximal end 101a of the drive housing 101 couples the drive housing 101 to a distal end 103a of the hand piece 103. A distal end 101b of the drive housing 101 couples to an insert portion 105. The insert portion 105 is configured to be inserted into an organ (e.g., a uterus) of a patient. According to some implementations, the insert portion 105 is a cutting blade (not shown) (e.g., a cutter) that extends into the patient. Alternatively, according to some implementations, the insert portion 105 accepts a cutting blade that extends into the patient.

Referring to FIG. 1B, FIG. 1B is an exploded view of the hand piece 103, according to some implementations of the present disclosure. The hand piece 103 includes a motor 131. The motor 131 drives (e.g., rotates) a shaft 133 according to an operation position (e.g., ON or OFF) of a switch 135. The switch 135 also allows for manual ON/OFF control of the suction and outflow. Although shown as a switch 135 on the hand piece 103, in some embodiments, the switch 135 can be a footswitch controlled by the foot of the operator of the surgical device 10. Surrounding the shaft 133 is an edge or ring 137.

Referring to FIG. 1C, FIG. 1C is an exploded view of the drive housing 101, according to some implementations of the present disclosure. The drive housing 101 includes an inner member 161 that is at least partially supported by and movable within an outer member 163 at the proximal end 101a. The inner member 161 and the outer member 163 together form a drive hub 101c of the drive housing 101. The inner member 161 includes a drive coupler 165 that couples to the shaft 133, such as an end of the shaft 133 (e.g., a fork), when the drive housing 101 couples to the hand piece 103. Operation of the motor 131 rotates the shaft 133, which rotates the drive coupler 165 and the inner member 161 relative to the outer member 163. That is, with the drive housing 101 coupled to the hand piece 103, the outer member 163 is rotatably fixed to the hand piece 103, and the inner member 161 is free to rotate within the drive housing 101. Rotation of the inner member 161 causes, for example, the cutting blade within the insert portion 105 to rotate to provide a cutting action.

During a procedure with the surgical device 10, fluid is aspirated from inside the patient by the surgical device 10. Accordingly, the drive housing 101, the hand piece 103, and the insert portion 105 include one or more lumen (not shown) to transport fluid (including fluid and material) from out of the patient (e.g., an organ of the patient, such as the uterus). The distal end of the insert portion 105 (e.g., at the cutting blade) includes an opening 107 that allows fluid to flow into the surgical device 10 based on suction. The hand piece 103 includes an outlet 109 at a proximal end 103*b* to allow the fluid to flow out of the surgical device 10. One or more lumen of the drive housing 101, the hand piece 103, and the insert portion 105 are in fluid communication with the opening 107 and the outlet 109 to transport the fluid through the surgical device 10.

At least one lumen is formed by the inner diameter of the inner member 161 within the proximal end 101*a* of the drive housing 101. Fluid flows from the insert portion 105 into the inner member 161. The fluid is aspirated from out of the inner member 161 through an opening 169. That is, the fluid flows out of the opening 169 when the opening 169 is aligned with a window 167 in the outer member 163. During operation of the surgical device 10, the inner member 161 rotates relative to the outer member 163, and the opening 169 periodically aligns with the window 167 to allow the fluid to flow out of the inner member 161. The outer diameter of the inner member 161 and the inner diameter of the outer member 163 are sized so that fluid is obstructed and/or blocked from flowing out of the inner member 161 when the opening 169 is not aligned with the window 167.

Although a single window 167 is shown on the outer member 163, in alternate embodiments, the outer member 163 can include more than one window 167. Further, although only one opening 169 is shown on the inner member 161, according to some implementations, the inner member 161 can include more than one opening 169. According to some implementations with multiple openings 169 and windows 167, the arrangement of the openings 169 and the windows 167 at least allows for the openings 169 to be aligned with the windows 167 in a first arrangement, and not aligned (or partially not aligned) with the windows in the second arrangement. The second arrangement resists and/or blocks the flow of fluid out of the inner member 161 based on the positions of the openings 169 relative to the windows 167.

Figure 2:
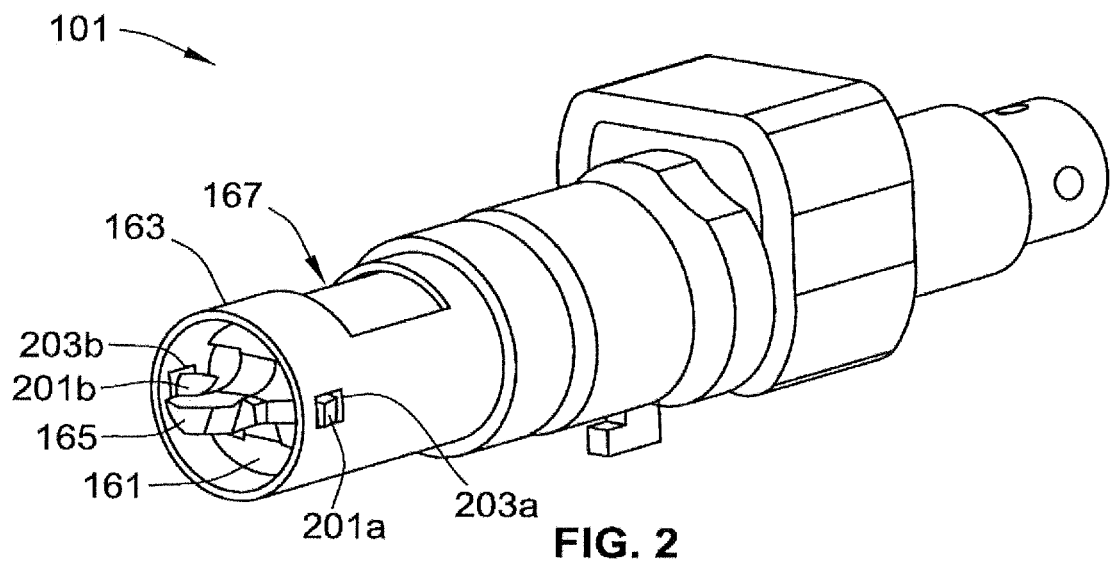
FIG. 2 is a detailed view of the drive housing, according to some implementations of the present disclosure.

Referring to FIG. 2, FIG. 2 illustrates a detailed view of the drive housing 101, according to some implementations of the present disclosure. As described with respect to FIGS. 1A-1C, the drive housing 101 includes the inner member 161 rotatably supported within the outer member 163. The outer member 163 includes the window 167. The inner member 161 includes the drive coupler 165 that couples to the shaft 133 (FIG. 1B) of the hand piece 103 when the hand piece 103 is coupled to the drive housing 101.

As described above, as the inner member 161 rotates within the outer member 163, the opening 169 (FIG. 1C) of the inner member 161 periodically aligns with the window 167 to allow fluid (or fluid and material) to flow out of the lumen formed by the inner member 161. When the opening 169 is not aligned with the window 167, as shown in FIG. 2, the flow is obstructed or blocked.

According to some implementations, the periodic alignment and misalignment of the opening 169 with the window 167 can be accomplished according to movements other than rotating the inner member 161 relative to the outer member 163. For example, according to some implementations, the inner member 161 can move linearly in a repetitive back and forth motion relative to the outer member 163. Alternatively, the inner member 161 can rock and/or tilt in an iterative, repetitive manner relative to the outer member 163. In alternate embodiments, the inner member 161 can perform a combination of any one or more motions relative to the outer member 163, such as rotating while also moving in a linear back and forth motion. Thus, although the present disclosure discusses rotation of an inner member relative to an outer member, and locking/unlocking such motion, the present disclosure applies to other types and/or combinations of motion of an inner member relative to an outer member, not limited to rotation, that allows for a periodic alignment of a window and an opening to allow a periodic flow of fluid.

In some embodiments, the locking elements 201*a* and 201*b* extend from the inner member 161 and engage openings 203*a* and 203*b* in the outer member 163. According to some implementations, the locking elements 201*a* and 201*b* can extend from the drive coupler 165. However, the locking elements 201*a* and 201*b* can extend from other positions on the inner member 161 without departing from the spirit and scope of the present disclosure.

When the locking elements 201*a* and 201*b* are engaged with the openings 203*a* and 203*b*, the inner member 161 is rotatably locked relative to the outer member 163. The locking elements 201*a* and 201*b* may be positioned on the inner member 161 such that, when engaged with the openings 203*a* and 203*b*, the opening 169 of the inner member 161 is not aligned with the window 167 of the outer member 163 to obstruct flow. Accordingly, when the locking elements 201*a* and 201*b* engaged with the openings 203*a* and 203*b*, fluid flow out of the inner member 161 is blocked or restricted.

Although illustrated and described as openings, the openings 203*a* and 203*b* may alternatively be indentations, ridges, grooves, or other features or combinations of features on the outer member 163 that are configured to engage the locking elements 201*a* and 201*b*.

According to some implementations of the present disclosure, the locking elements 201*a* and 201*b* may instead be on the outer member 163 and extend towards the inner member 161. In alternate embodiments, the openings 203*a* and 203*b* may instead be on the inner member 161 and engage the locking elements 201*a* and 201*b* extending from the outer member 163.

According to some embodiments of the present disclosure, the inner member 161 can include only one locking element 201 (as shown in FIG. 1C) and the outer member 163 can include only one opening 203 (as shown in FIG. 1C). In alternate embodiments, according to some implementations, the inner member 161 can include more than two locking elements 201 and the outer member 163 can include more than two openings 203. Additionally, in implementations with multiple locking elements 201 and openings 203, a subset of locking elements 201 can be located on and extend from the inner member 161, and a remaining subset of locking elements 201 can be located on and extend from the outer member 163. Consequently, a subset of openings 203 can be on the outer member 163, and a remaining subset of openings 203 can be on the inner member 161.

Figure 3A:
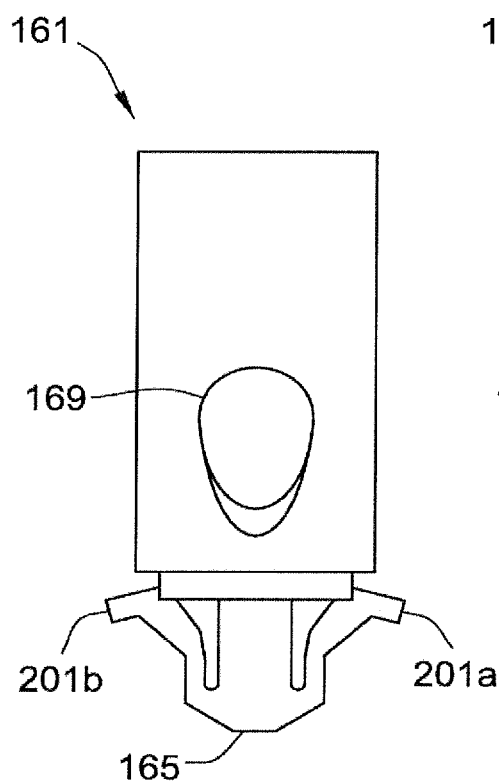
FIGS. 3A and 3B are top views of an inner member, according to some implementations of the present disclosure.
Figure 3B:
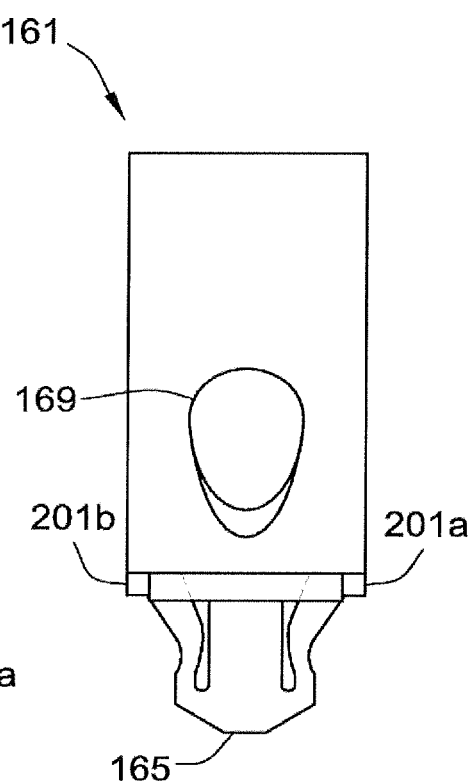

FIGS. 3A and 3B are top views of the inner member 161, according to some implementations of the present disclosure. Referring to FIG. 3A, the two locking elements 201*a* and 201*b* can extend from opposite sides of the drive coupler 165. FIG. 3A illustrates the inner member 161 and the locking elements 201*a* and 201*b* in a locked arrangement with the outer member 163 (not shown), such as with the locking elements 201*a* and 201*b* extending beyond the outer diameter of the inner member 161. Although not shown, in the arrangement illustrated in FIG. 3A, the locking elements 201*a* and 201*b* engage the openings 203*a* and 203*b* in the outer member 163 and resist the inner member 161 from rotating relative to the outer member 163.

FIG. 3B illustrates the locking elements 201a and 201b in an unlocked arrangement, such as with the locking elements 201a and 201b not extending beyond the outer diameter of the inner member 161. Although not shown, in the arrangement illustrated in FIG. 3B, the locking elements 201a and 201b do not engage the openings 203a and 203b in the outer member 163, which permits the inner member 161 to rotate relative to the outer member 163.

The locking elements 201a and 201b are bendable flexural arms configured to change from the first arrangement of FIG. 3A to the second arrangement of FIG. 3B, according to some implementations, the locking elements 201a and 201b are bendable flexural arms. However, the shape and configuration of the locking elements 201a and 201b can vary without departing from the spirit and scope of the present disclosure. Upon coupling the drive housing 101, including the inner member 161 and the outer member 163, to the hand piece 103, the ring 137 on the hand piece 103 which surrounds the shaft 133 engages the locking elements 201a and 201b while in the first arrangement of FIG. 3A and forces the locking elements 201a and 201b to flex according to the second arrangement of FIG. 3B. That is, the ring 137 of the hand piece 103 forces the locking elements 201a and 201b to disengage from the openings 203a and 203b, which rotatably unlocks the inner member 161 relative to the outer member 163.

Figure 4:
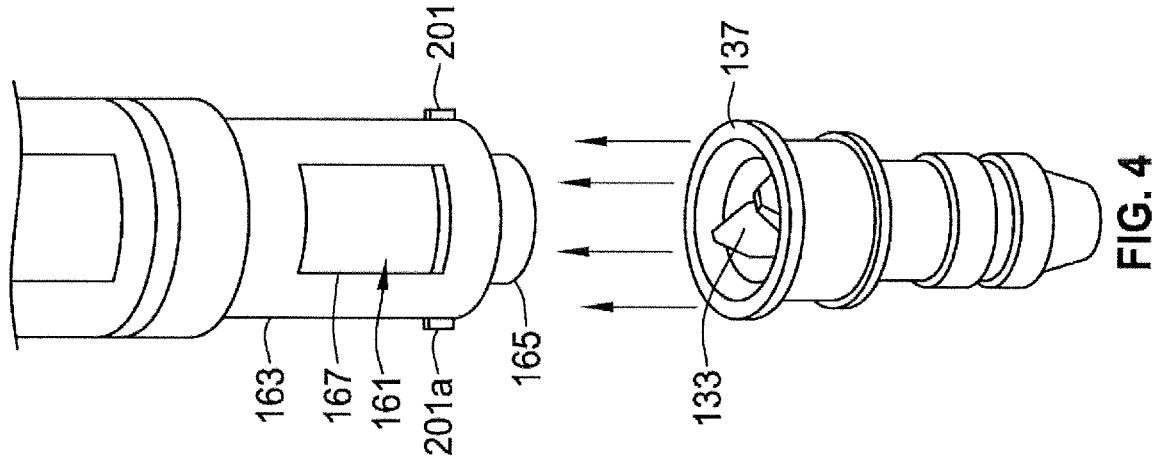
FIG. 4 is a perspective view of a coupling of a drive housing and a hand piece, according to some implementations of the present disclosure.

Accordingly, the drive housing 101 is initially assembled with the inner member 161 and locking elements 201a and 201b in the first arrangement engaged with openings 203a and 203b of the outer member 163, and the opening 169 locked in misalignment with the window 167. By being assembled in the first arrangement, the inner member 161 cannot rotate relative to the outer member 163 such that the opening 169 cannot align with the window 167. Accordingly, the drive housing 101 is maintained in an arrangement that obstructs aspiration of fluid (or fluid and material) through the inner member 161 prior to coupling the drive housing 101 to the hand piece 103. Referring to FIG. 4, coupling the drive housing 101 to the hand piece 103 brings the ring 137 surrounding the shaft 133 into engagement with the locking elements 201a and 201b, which unlocks the opening 169 from misalignment with the window 167 and allows the hand piece 103 to drive the inner member 161. According to the foregoing, the drive housing 101 can be assembled in the first arrangement. In the first arrangement, a user (e.g., doctor, clinician, technician, etc.) of the drive housing 101 does not need to manually control the position of the opening 169 relative to the window 167 prior to using the drive housing 101, such as prior to coupling the drive housing 101 to the hand piece 103, prior to inserting the insert portion 105 connected to the drive housing 101 into the patient, or after inserting the insert portion 105 into the patient. According to some implementations, the user also does not need to manually control the position of the opening 169 relative to the window 167 prior to withdrawing the insert portion 105 from within the patient. Unwanted fluid loss as a result of uncontrolled aspiration of fluid is reduced or prevented because the opening 169 is blocked by the window 167 upon connecting the drive housing 101 to the hand piece 103 and/or withdrawing the insert portion 105 from the patient.

In alternate embodiments, the locking elements 201a and 201b can be positioned on the inner member 161 such that, when engaged with the openings 203a and 203b, the inner member 161 is in a position that causes the opening 107 at the distal end of the insert portion (e.g., an opening of a cutting blade) to be in a closed position. Accordingly, the aspiration of fluid (or fluid and tissue) can be reduced or prevented at the opening 107 of the insert portion 105, in addition or in the alternative to having the opening 169 being misaligned with the window 167 and blocked by the outer member 163. Similar arrangements with respect to the opening 107 being obstructed or blocked apply to the additional implementations of the present disclosure discussed below.

FIG. 5 illustrates an inner member 501 and an outer member 503 arrangement of a drive housing 500, according to additional implementations of the present disclosure. The drive housing 500 includes the inner member 501 rotatably supported by within the outer member 503. The inner member 501 can further translate relative to the outer member 503 along the rotational axis 505 of the inner member 501 within the drive housing 500.

The inner member 501 includes a groove 507 in an outer surface that extends around the entire outer circumference of the inner member 501. The inner member 501 also includes a recess 509 within a portion of the outer circumference of the inner member 501. At least a portion of the groove 507 is in communication with the recess 509.

Figure 5B:
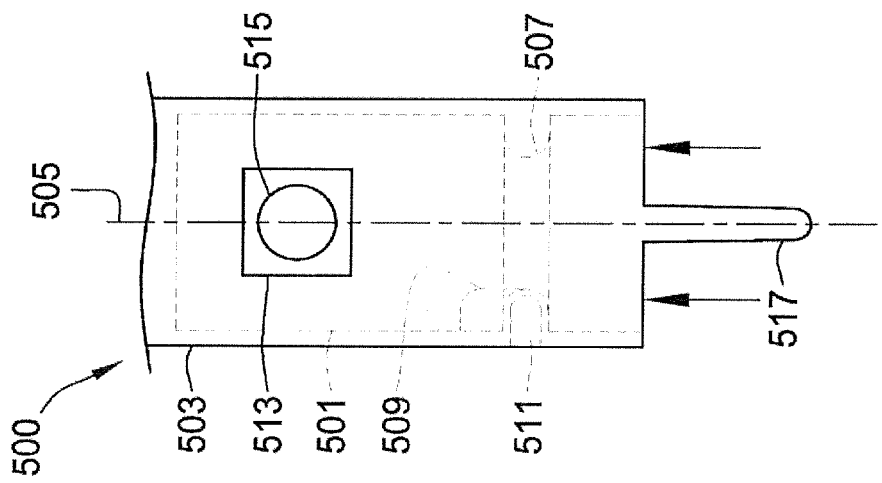
FIGS. 5A and 5B are top views of a proximal end of a drive housing, according to additional implementations of the present disclosure.

The outer member 503 includes a protrusion 511 that extends inward from the inner surface of the outer member 503. The outer member 503 also includes a window 513, and the inner member 501 includes an opening 515 (FIG. 5B). When the opening 515 is aligned with the window 513, fluid (or fluid and material) flows from out of the inner member 501 and out of the opening 515 through the window 513. When the opening 515 is not aligned with the window 513, the inner surface of the outer member 503 obstructs or blocks fluid from flowing out of the opening 515.

Figure 5A:
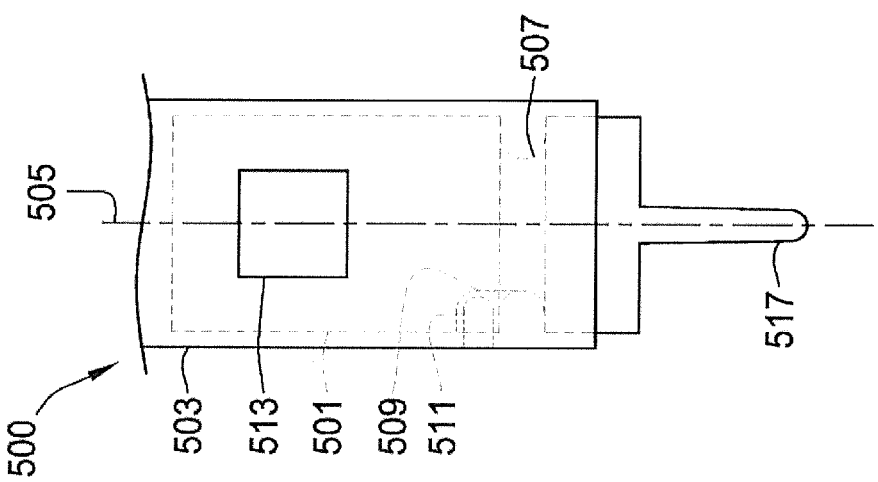

In a first arrangement, illustrated in FIG. 5A, the protrusion 511 engages the recess 509, which rotatably locks the inner member 501 relative to the outer member 503. The recess 509 is positioned on the inner member 501 such that, when the protrusion 511 engages the recess 509, the opening 515 in the inner member 501 is not aligned with the window 513. Accordingly, in the first arrangement, flow is obstructed and/or blocked.

In a second arrangement, illustrated in FIG. 5B, the protrusion 511 engages the groove 507, which permits the inner member 501 to rotate relative to the outer member 503. In the second arrangement, a hand piece (e.g., hand piece 103) can rotate the drive coupler 517 and the inner member 501 relative to the outer member 503. Accordingly, in the second arrangement, flow is permitted by the opening 515 periodically aligning with the window 513 based on the hand piece 103 rotating the inner member 501.

The drive housing 500 is assembled according to the first arrangement illustrated in FIG. 5A. Because the inner member 501 can translate relative to the outer member 503 along the axis 505, coupling the drive housing 500 to the hand piece 103 causes the protrusion 511 on the outer member 503 to move from being engaged with the recess 509 to being within the groove 507 because the inner member 501 translates relative to the outer member 503 in the direction of the arrows in FIG. 5B. Thus, coupling the hand piece 103 to the drive housing 500 unlocks the inner member 501 relative to the outer member 503 and unlocks the opening 515 relative to the window 513.

Accordingly, the drive housing 500 is maintained in an arrangement that obstructs or blocks fluid (or fluid and material) from flowing out of the inner member 501 prior to coupling the drive housing 500 to the hand piece 103.

Therefore, an operator of a surgical device (e.g., surgical device 10) that includes the drive housing 500 does not need to manually misalign the opening 515 with the window 513 prior to coupling the drive housing 500 to the hand piece 103, or prior to inserting an insert portion (e.g., insert portion 105) of the surgical device 10 comprising the drive housing 500 into the patient.

Figure 6B:
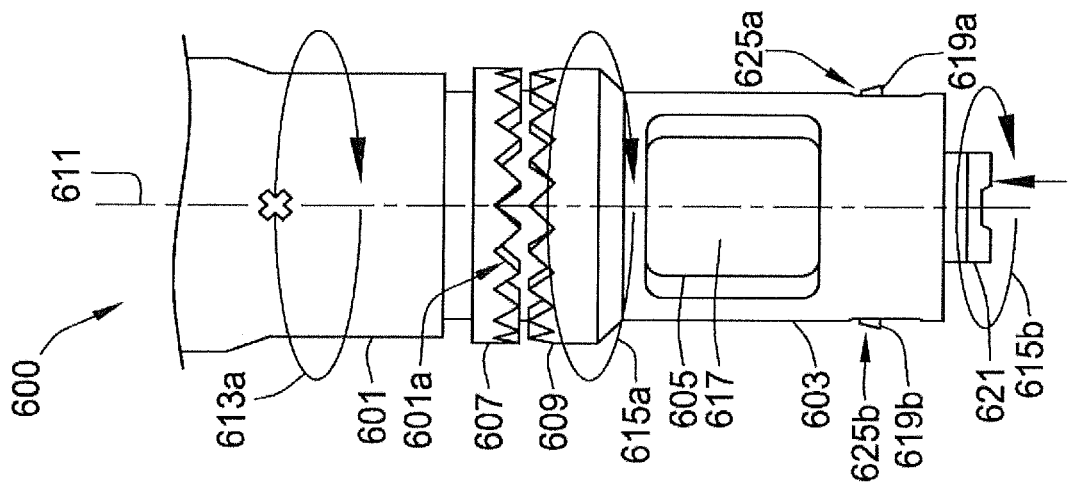
Figure 6A:
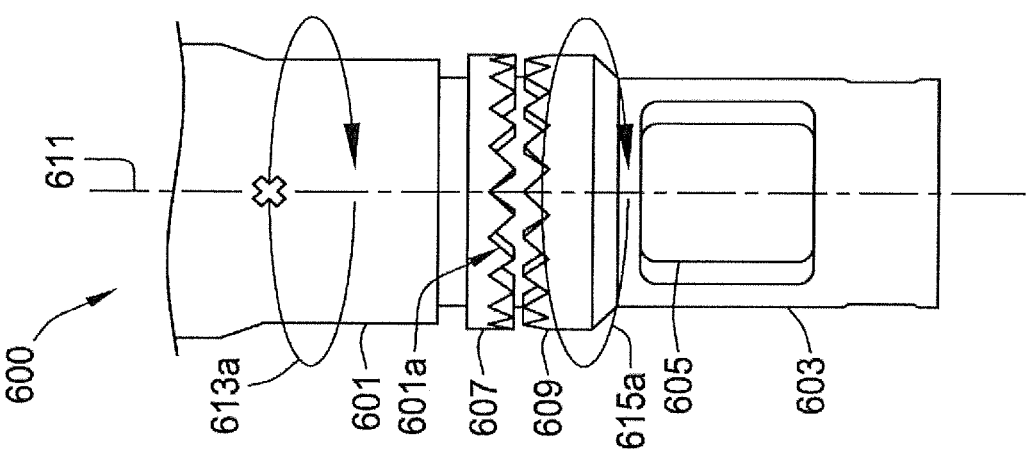

FIGS. 6A-6D illustrate a drive housing 600 that can replace the drive housing 101 of the surgical device 10, according to additional implementations of the present disclosure. Referring to FIG. 6A, the drive housing 600 includes an outer member 601 and a free member 603. Both the outer member 601 and the free member 603 are hollow to allow fluid to pass therethrough. The free member 603 overlaps a proximal end 601a of the outer member 601 such that the free member 603 is rotatably supported by the outer member 601 at the proximal end 601a. The free member 603 includes a window 605.

The proximal end 601a of the outer member 601 facing the free member 603 includes a proximal castellated region 607. The distal end of the free member 603 facing the outer member 601 includes a distal castellated region 609. The free member 603 translates about the axis of rotation 611 relative to the outer member 601 to allow the proximal castellated region 607 to engage/disengage the distal castellated region 609. With the proximal castellated region 607 and the distal castellated region 609 engaged, the outer member 601 and the free member 603 are rotationally locked. With the proximal castellated region 607 and the distal castellated region 609 disengaged, the outer member 601 and the free member 603 are rotationally unlocked, as illustrated by the locked arrow 613a relating to the outer member 601 relative to the unlocked arrow 615a relating to the free member 603 in FIG. 6A.

Referring to FIG. 6B, an inner member 617 is rotationally supported by one or both of the outer member 601 and the free member 603, and extends through the outer member 601 and the free member 603. According to some implementations, the inner member 617 of FIG. 6B can be identical to the inner member 161 such that the inner member 617 includes locking elements 619a and 619b and a drive coupler 621, which are similar to locking elements 201a and 201b and drive coupler 165. The inner member 617 further includes an opening 623 (FIG. 6D) that allows fluid (or fluid and tissue) to pass out of the inner member 617 and through the window 605 of the free member 603, when the opening 623 and the window 605 are aligned.

The free member 603 includes openings 625a and 625b that engage the locking elements 619a and 619b. The locking elements 619a and 619b are positioned on the inner member 617 such that, when the locking elements 619a and 619b engage the openings 625a and 625b, the opening 623 is blocked by the free member 603 and not aligned with the window 605.

Alternatively, as discussed with respect to FIGS. 2, 3A, and 3B, according to some implementations of the present disclosure, the inner member 617 can include one or more locking elements 619a and 619b, and the free member 603 can include one or more openings 625a and 625b. Additionally, in implementations with multiple locking elements 619 and openings 625, a subset of locking elements 619 can be located on and extend from the inner member 617, and a remaining subset of locking elements 619 can be located on and extend from the free member 603. Consequently, a subset of openings 625 can be on the free member 603, and a remaining subset of openings 625 can be on the inner member 617. Further, although described as an opening, the openings 625a and 625b can alternatively be an indentation, a ridge, a groove, or other feature on the free member 603 (or inner member 617) that is configured to engage the locking elements 619a and 619b.

With the locking elements 619a and 619b engaged with the openings 625a and 625b according to a first arrangement, the inner member 617 is rotationally locked relative to the free member 603. Further, with the proximal castellated region 607 and the distal castellated region 609 disengaged, the inner member 617 is not rotationally locked with the outer member 601, as illustrated with respect to unlocked arrow 615b. In this example arrangement, the inner member 617 is free to rotate relative to the outer member 601. Accordingly, the drive coupler 621 can rotate upon contacting the shaft 133 of a hand piece (e.g., the hand piece 103) when coupling the drive housing 600 to the hand piece 103. According to this example arrangement, the start/stop or home position of the shaft 133 of the hand piece 103 can be recognized, and the shaft 133 does not need to be rotated to connect the hand piece 103 to the drive housing 600. Because the start/stop or home position of the shaft 133 of the hand piece 103 can be recognized, the motor 131 of the hand piece 103 can track the starting and stopping points of the inner member 617 and can stop rotation of the inner member 617 so that the opening 623 of the inner member 617 stops rotating in a blocked position by the free member 603. Accordingly, both a starting point and a stopping point of using the surgical device 10 within a patient can obstruct or block aspiration of fluid (or fluid and tissue) to reduce or prevent unwanted fluid loss and/or distorted views caused by turbulence.

Referring to FIG. 6C, FIG. 6C shows the proximal castellated region 607 engaged with the distal castellated region 609. With the locking elements 619a and 619b engaged with the openings 625a and 625b, and the proximal castellated region 607 engaged with the distal castellated region 609, the inner member 617 is rotationally locked with the free member 603 and the outer member 601, as illustrated by locked arrows 613b and 613c. The proximal castellated region 607 and the distal castellated region 609 engage when the free member 603 and the inner member 617 translate toward the outer member 601 along the axis of rotation 611. The translation occurs upon bringing the hand piece 103 into contact with the free member 603 and the inner member 617. As shown in FIGS. 6A-6D, the castellated regions 607 and 609 are on the outside of the outer member 601 and the free member 603, respectively, and are visible to, for example, the user (e.g., operator) of the drive housing 600.

Further, and as discussed with respect to FIG. 4 above, upon coupling the hand piece 103 to the inner member 617 and the free member 603, the ring 137 (not shown in FIG. 6C for illustrative convenience) of the hand piece 103 forces the locking elements 619a and 619b of the inner member 617 from a first arrangement, engaged with the openings 625a and 625b, as shown in FIG. 6C, to a second arrangement, disengaged with the openings 625a and 625b, as shown in FIG. 6D. According to the second arrangement, as illustrated in FIG. 6D, the inner member 617 can rotate relative to the free member 603, with the free member 603 rotationally locked with the outer member 601. Thus, coupling the hand piece 103 to the inner member 617 causes the locking elements 619a and 619b of the inner member 617 to disengage, which allows the hand piece 103 to drive the inner member 617.

Accordingly, the drive housing 600 is initially assembled with the inner member 617 and the locking elements 619a and 619*b* in the first arrangement with the free member 603 and the openings 625*a* and 625*b*, and the opening 623 locked in misalignment with the window 605 of the free member 603. By being assembled in the first arrangement, a user of the surgical device 10 does not need to manually lock the drive housing 600 by misaligning the opening 623 with the window 605. The drive housing 600 assembled in the first arrangement obstructs or blocks fluid (or fluid and material) from flowing out of the inner member 617. Coupling the drive housing 600 to the hand piece 103, as illustrated in FIG. 6D, unlocks the locking elements 619*a* and 619*b* from the openings 625*a* and 625, which allows the hand piece 103 to drive the inner member 617. Driving the inner member 617 allows the opening 623 to be periodically aligned with the window 605 to allow fluid (or fluid and material) to flow out of the inner member 617. According to the foregoing, the drive housing 600 can be assembled in the first arrangement such that a user of the drive housing 600 (e.g., doctor, clinician, technician, etc.) does not need to manually lock the drive housing 600 prior to coupling the drive housing 600 to a hand piece, or prior to inserting an insert portion coupled to the drive housing into a patient, while still obstructing unwanted fluid loss.

FIG. 7 shows a drive housing 700 including an alternative arrangement to the drive housing 600, according to some implementations of the present disclosure. Referring to FIG. 7, rather than including the distal castellated region 609 at the distal end, the free member 603 can include a castellated region 701 proximal to the distal end of the free member 603. Similarly, rather than having the proximal castellated region 607 of the outer member 601 distal to the proximal end of the outer member 601, the outer member 601 can include a castellated region 703 on the proximal end of the outer member 601. The distal end of the free member 603 further can include an O-ring 705 that closes the distal end of the free member 603 relative to the outer member 601. The O-ring 705 can be formed of a soft elastic material that can act as a spring. The arrangement of the drive housing 700 can otherwise be the same or similar to the arrangement of the drive housing 600 of FIGS. 6A-6D. In contrast to the drive housing 600, the castellated regions 703 and 701 are on the outside of the outer member 601 and the free member 603, respectively, and are not visible to, for example, the operator of the drive housing 700 based on being enclosed by, for example, the O-ring 705.

Figure 8:
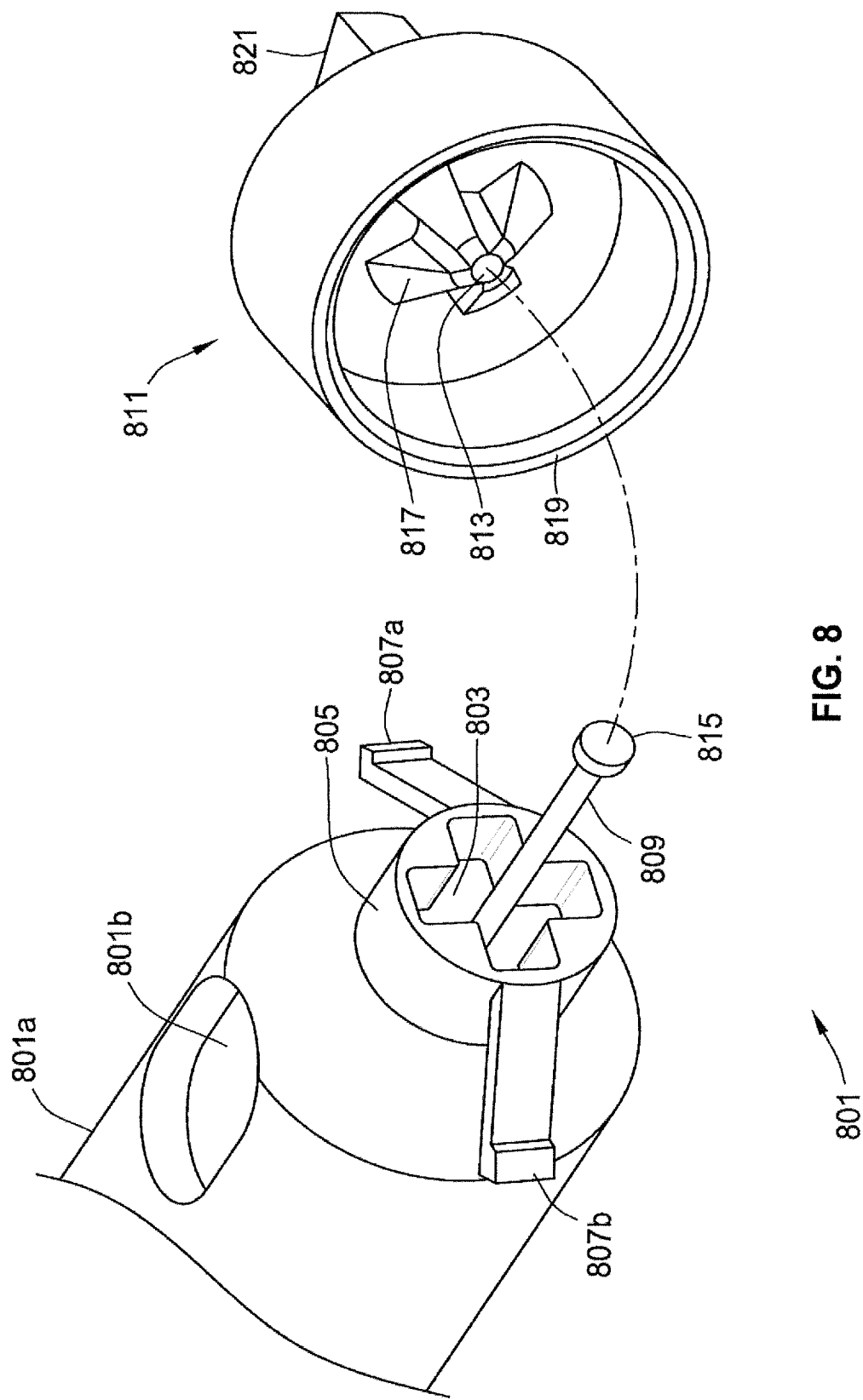
FIG. 8 is a perspective view of an inner member, according to some additional implementations of the present disclosure.

FIG. 8 is a perspective view of an inner member 801, according to additional implementations of the present disclosure. The inner member 801 includes a main body 801*a*. Similar to the inner members discussed above, the inner member 801 includes an opening 801*b* within the main body 801*a* that allows fluid to flow out of the inner portion of the inner member 801.

The inner member 801 also includes a recess 803 within a neck 805 at a proximal end. Alternatively, the inner member 801 can have the recess 803 directly within the proximal end, without including the neck 805. The recess 803 can be formed to have a specific shape, such as the shape of Phillips-head or crosshead. However, the shape of the recess 803 can vary without departing from the spirit and scope of the present disclosure.

Similar to the inner member 161, locking elements 807*a* and 807*b* extend from the neck 805. Further, a shaft 809 extends from a center of the recess 803 and is configured to accept a drive coupler 811 via a hole 813 within the drive coupler 811 that fits around the shaft 809. The shaft 809 further includes an end 815 that resists the drive coupler 811 from sliding off of the shaft 809.

The drive coupler 811 includes a protrusion 817. The shape of the protrusion 817 is configured to complement the shape of the recess 803. However, alternatively, the inner member 801 can include the protrusion 817 and the drive coupler 811 can include the recess 803. The drive coupler 811 also includes a flange 821 that engages with a shaft (e.g., shaft 133) of a hand piece (e.g., hand piece 103).

The protrusion 817 engages the recess 803 when the drive coupler 811 is at the distal end of the shaft 809 and rotationally locks the drive coupler 811 to the inner member 801 based on the complementary shapes of the recess 803 and the protrusion 817. When the drive coupler 811 is not at the distal end of the shaft 809, the protrusion 817 does not engage the recess 803 and the drive coupler 811 is free to rotate about the shaft 809 relative to the inner member 801.

The inner member 801 can be used in one or more of the drive housings disclosed herein as a replacement of the inner member. By way of example, like the inner member 161 of FIG. 2, the inner member 801 can be rotatably supported within an outer member, and, in a first arrangement, the locking elements 807*a* and 807*b* rotationally lock the inner member 801 relative to the outer member. However, according to the configuration described above, the drive coupler 811 is free to rotate about the shaft 809 despite the inner member 801 being rotationally locked relative to the outer member when the protrusion 817 is not engaged with the recess 803.

Figure 9B:
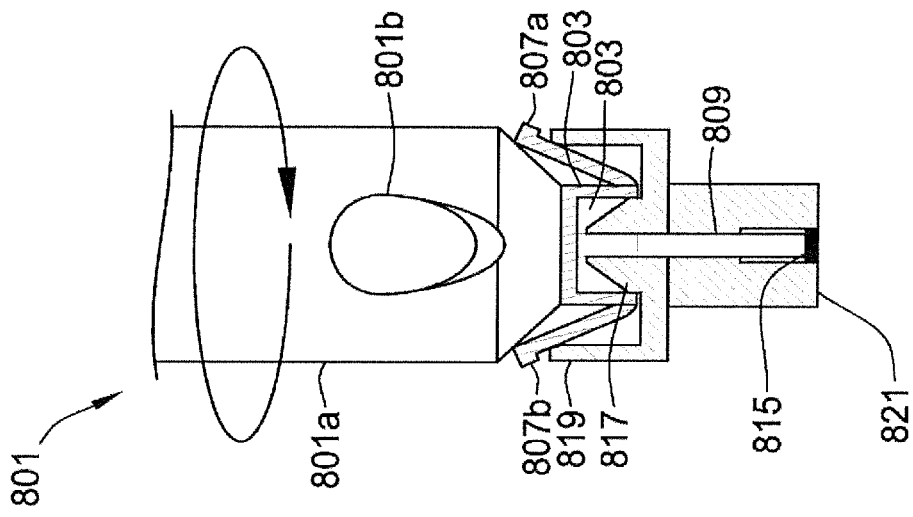
FIGS. 9A and 9B are top views of the inner member of FIG. 8, according to some implementations of the present disclosure.
Figure 9A:
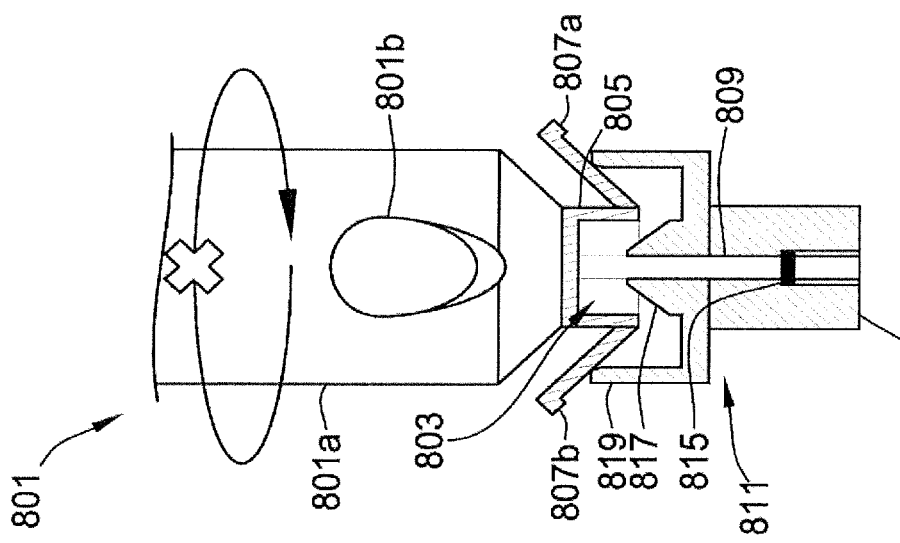

FIGS. 9A and 9B show a first arrangement (FIG. 9A) and a second arrangement (FIG. 9B) of the inner member 801, according to some implementations of the present disclosure. As shown in FIG. 9A, the inner member 801 is in a first arrangement with the protrusion 817 not engaged with the recess 803. In the first arrangement, the drive coupler 811 is free to rotate about the shaft 809 relative to the main body 801*a* of the inner member 801. The locking elements 807*a* and 807*b*, however, can be engaged with openings in an outer member (not shown) rotatably supporting the inner member 801, to lock the main body 801*a* of the inner member 801 rotationally relative to the outer member.

Referring to FIG. 9B, upon coupling a hand piece 103 to the inner member 801 with the inner member 801 within a drive housing (e.g., drive housing 101), the shaft 133 of the hand piece 103 engages with the flange 821 and forces the drive coupler 811 towards the distal end of the shaft 809. Upon the drive coupler 811 reaching the distal end of the shaft 809, the protrusion 817 engages the recess 803. Further, the rim 819 of the drive coupler 811 contacts the locking elements 807*a* and 807*b* and causes the locking elements 807*a* and 807*b* to disengage from the first arrangement such that the inner member 801 becomes rotationally free relative to an outer member. With the protrusion 817 engaged with the recess 803, the hand piece 103 can rotate the inner member 801 relative to the outer member to operate a surgical device.

According to the drive coupler 811 initially being free to rotate relative to the inner member 801 prior to the hand piece 103 being coupled to the inner member 801, the drive coupler 811 is free to rotate to align the flange 821 with the shaft 133 of the hand piece 103. With this example arrangement, the start/stop or home position of the shaft 133 of the hand piece 103 can be recognized, and the shaft 133 does not need to be rotated to connect the hand piece 103 to the inner member 801. Because the start/stop or home position of the shaft 133 of the hand piece 103 can be recognized, the motor 131 of the hand piece 103 can track the starting and stopping points of the inner member 801 and can stop rotation of the inner member 801 so that the opening 801*b* of the inner member 801 stops rotating in a blocked position the outer member (e.g., not aligned with a window in the outer member). Accordingly, a stopping point of using the surgical device, including the inner member 801, can block aspiration of fluid (or fluid and tissue) to reduce or prevent unwanted fluid loss and/or distorted views caused by turbulence after stopping the rotation.

Figure 10G:
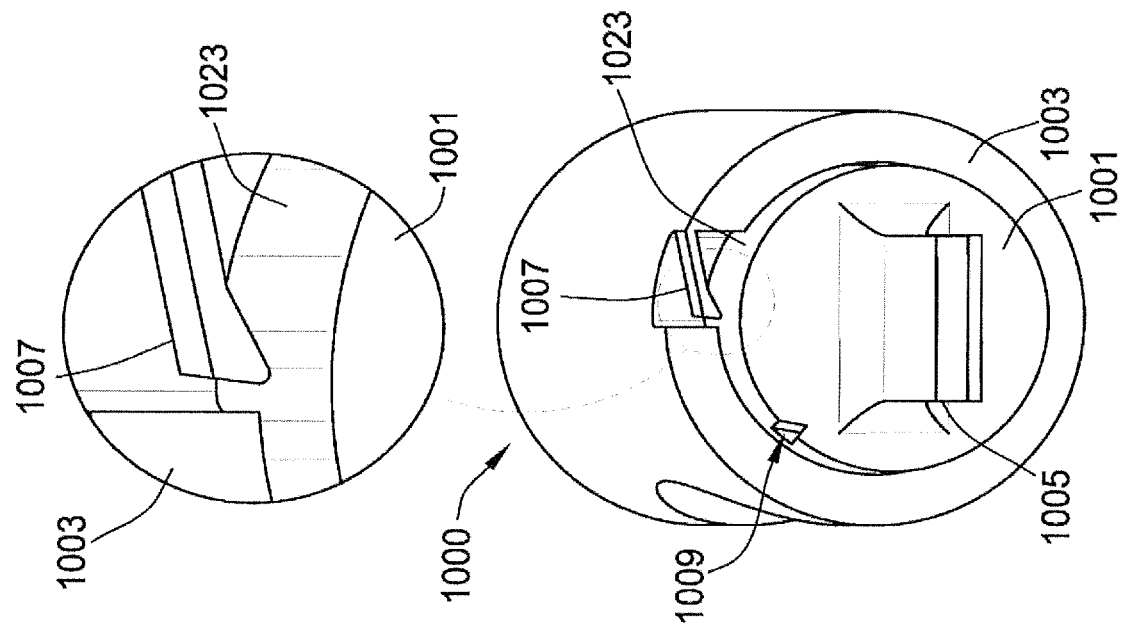
FIGS. 10F and 10G are end views of the drive housing illustrated in FIGS. 10A through 10C, according to some additional implementations of the present disclosure.

FIGS. 10A-10I show a drive hub 1000 of a drive housing, according to additional implementations of the present disclosure. Specifically, FIGS. 10A-10C, 10F, and 10G-10I show perspective views of a proximal end of the drive hub 1000. FIGS. 10D and 10E show top-down views of the drive hub 1000 in FIGS. 10A-10C. Referring to FIG. 10A, the drive hub 1000 includes an inner member 1001 rotatably supported within an outer member 1003. The inner member 1001 includes a drive coupler 1005 for coupling the inner member 1001 to a shaft (e.g., shaft 133) of a hand piece (e.g., hand piece 103) to rotate the inner member 1001.

The outer member 1003 includes a flexible arm 1007 that extends from the outer member 1003. The flexible arm 1007 can be formed of various materials, such as the material of the outer member 1003 and/or one or more additional materials, such as metals, plastics, rubber, etc. According to a first arrangement, the flexible arm 1007 extends into a recess 1009 in the outer surface of the inner member 1001. With the flexible arm 1007 extending into the recess 1009 in the first arrangement, the flexible arm 1007 engages a surface 1011a partially defining the recess 1009 when the inner member 1001 is rotated (or is attempted to be rotated) clockwise relative to the outer member 1003 (e.g., FIG. 10A). Thus, the surface 1011a resists the inner member 1001 from being rotated clockwise with the flexible arm 1007 extending into the recess 1009 in the first arrangement.

When the inner member 1001 is rotated counterclockwise relative to the outer member 1003 in the first arrangement, the surface 1011b partially defining the recess 1009 contacts the flexible arm 1007 (FIG. 10B). The flexible arm 1007 applies a threshold resistance to resist further rotating the inner member 1001 counterclockwise. However, a sufficient force exceeds the threshold resistance generated by the flexible arm 1007 against the surface 1011b and the surface 1011b causes the flexible arm 1007 to flex, which permits the inner member 1001 to rotate at least one rotation in a counterclockwise direction relative to the outer member 1003 (FIG. 10C). The threshold resistance can be sufficient to resist the inner member 1001 from freely rotating in the counterclockwise direction unless the inner member 1001 is coupled to a hand piece 103. By way of example, when coupled to a hand piece 103, the hand piece 103 can provide the sufficient force to exceed the threshold resistance applied by the flexible arm 1007 and cause the flexible arm 1007 to flex.

The flexible arm 1007 and the recess 1009 are positioned on the outer member 1003 and the inner member 1001, respectively, such that, when the flexible arm 1007 engages the recess 1009, an opening 1017 (FIG. 10E) in the inner member 1001, which allows fluid to pass out of (or into) the inner member 1001 is blocked by the outer member 1003 or not aligned with a window 1019 (FIG. 10D) in the outer member 1003.

Accordingly, the flexible arm 1007 and the recess 1009 engage to maintain the inner member 1001 and the outer member 1003 in the first arrangement to obstruct fluid flow through the opening 1017. The flexible arm 1007 and the recess 1009 engaging resists the inner member 1001 from rotating clockwise relative to the outer member 1003 and resists the opening 1017 from becoming aligned with the window 1019 in response to a clockwise movement of the inner member 1001 relative to the outer member 1003. Further, the threshold resistance of the flexible arm 1007 engaged with the recess 1009 resists the inner member 1001 from rotating counterclockwise relative to the outer member 1003 and resists the opening 1017 from becoming aligned with the window 1019 in response to a counterclockwise movement of the inner member 1001 relative to the outer member 1003. When a sufficient force is applied on the flexible arm 1007, such as by a force applied by rotation of the shaft 133 of an attached hand piece 103, the flexible arm 1007 flexes and allows the inner member 1001 to rotate clockwise for at least one rotation, or at least during application of the sufficient force.

Based on the foregoing, the drive hub 1000 can be assembled with the flexible arm 1007 inserted into the recess 1009 and the opening 1017 in the inner member 1001 not aligned with a window 1019 in the outer member 1003. According to this example arrangement, fluid is obstructed or blocked from flowing out of (or into) the inner member 1001 through the opening 1017 of the inner member 1001 and the window 1019 of the outer member 1003. By engaging the surface 1011a and requiring a threshold force to flex, the flexible arm 1007 resists the inner member 1001 from rotating relative to the outer member 1003 and the opening 1017 from becoming aligned with the window 1019 in the outer member 1003 until a hand piece 103 is connected to the drive hub 1000. Accordingly, proper fluid and suction control can be maintained upon inserting a surgical device (e.g., surgical device 10) into a patient with the opening 1017 in a closed position and without a user of the surgical device 10 having to manually close the opening 1017. Moreover, with the recess 1009 resisting clockwise rotation of the inner member 1001 relative to the outer member 1003, the drive coupler 1005 can rotate the shaft 133 of the hand piece 103 to align and couple the hand piece 103 to the drive hub 1000. That is, the flexible arm 1007 resisting the inner member 1001 from rotating in a clockwise arrangement allows an operator to use the drive coupler 1005 to rotate the shaft 133 of the hand piece 103 into alignment with the inner member 1001, while not changing the position of the opening 1017 relative to the window 1019.

In an embodiment, the arrangement of the flexible arm 1007 and the recess 1009 is described above with respect to allowing counterclockwise rotation of the inner member 1001 upon the application of a sufficient force and resisting clockwise rotation of the inner member 1001. In an alternate embodiment, the arrangement of the flexible arm 1007 can change to allow the reverse rotational relationship, without departing from the spirit and scope of the present disclosure.

In some embodiments, the inner member 1001 is locked longitudinally with respect to the outer member 1003 along the axis of rotation. In alternate embodiments, the inner member 1001 is configured to translate about the axis of rotation relative to the outer member 1003. The translation of the inner member 1001 relative to the outer member 1003 allows the recess 1009 to translate relative to the flexible arm 1007.

Figure 10F:
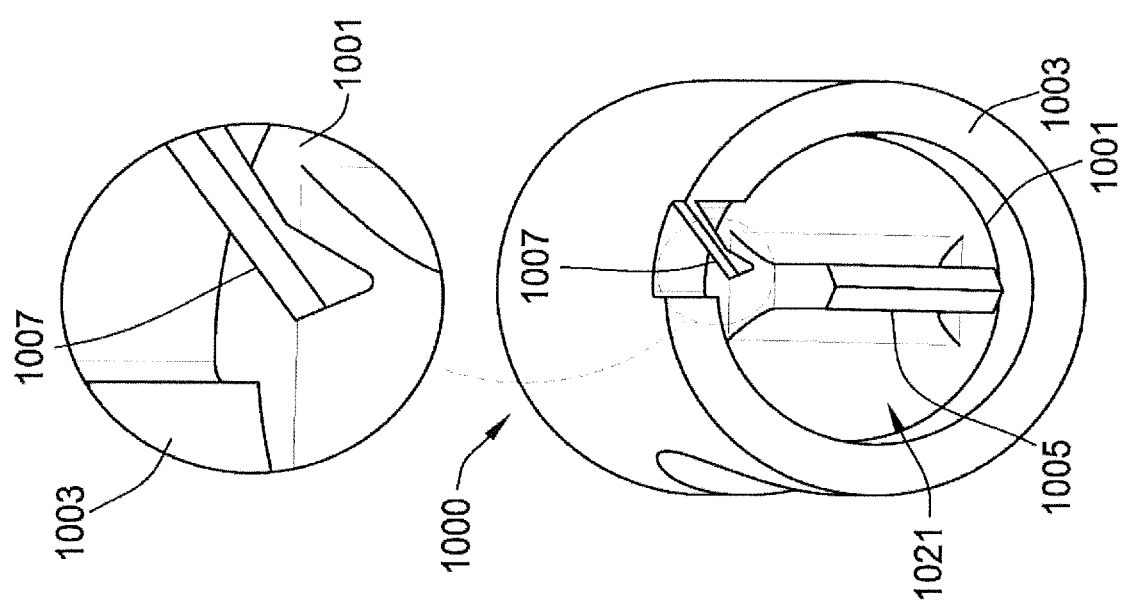

Referring to FIG. 10F, according to some implementations, the inner member 1001 can be configured to partially translate into the outer member 1003 such that the flexible arm 1007 fully extends beyond the circumferential edge of the inner member 1001 and engages the proximal surface 1021 of the inner member 1001. In such an arrangement, the inner member 1001 is free to rotate clockwise and counterclockwise relative to the outer member 1003. Further, such an arrangement resists the inner member 1001 from being withdrawn from the outer member 1003 by engaging the proximal surface 1021 of the inner member 1001. By way of example, and without limitation, such an arrangement can be configured to occur based on the drive hub 1000 engaging a hand piece (e.g., hand piece 103) and the hand piece causing the inner member 1001 to translate into the outer member 1003.

Referring to FIG. 10G, according to some implementations, the inner member 1001 can be configured to partially translate out of the outer member 1003 such that the flexible arm 1007 engages the circumferential edge 1023 of the inner member 1001 and does not re-engage with the recess 1009 upon the inner member 1001 rotating. By way of example, and without limitation, such an arrangement as shown in FIG. 10G can be configured to occur based on the drive hub 1000 engaging a hand piece (e.g., hand piece 103) and the hand piece causing the inner member 1001 to translate out of the outer member 1003.

Figure 10I:
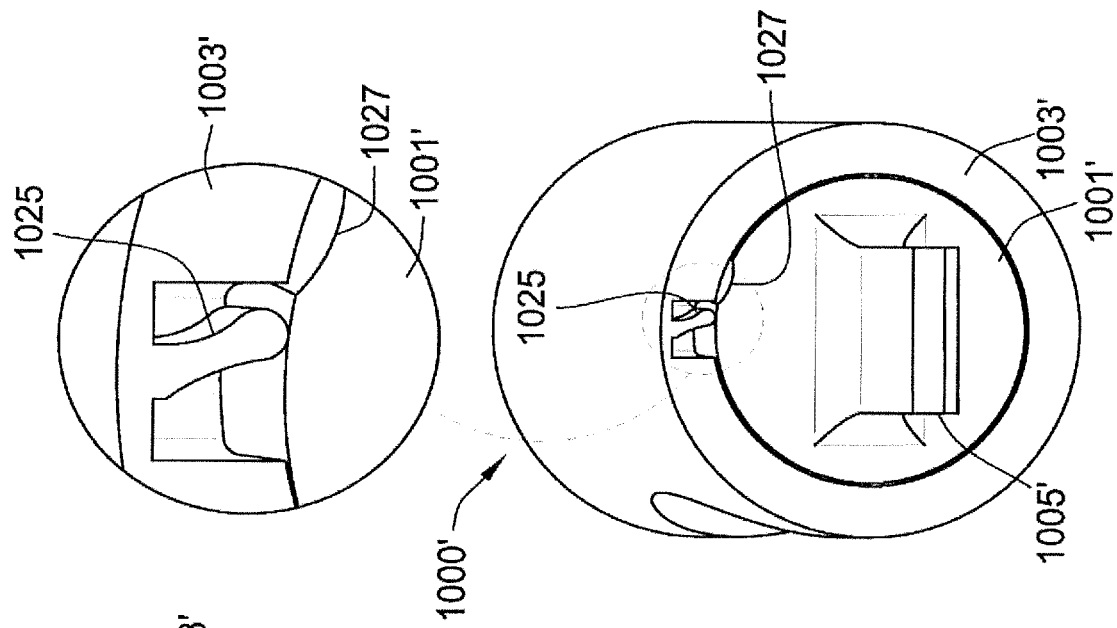
FIGS. 10H and 10I are end views of the drive housing illustrated in FIGS. 10A through 10C, according to some additional implementations of the present disclosure.
Figure 10H:
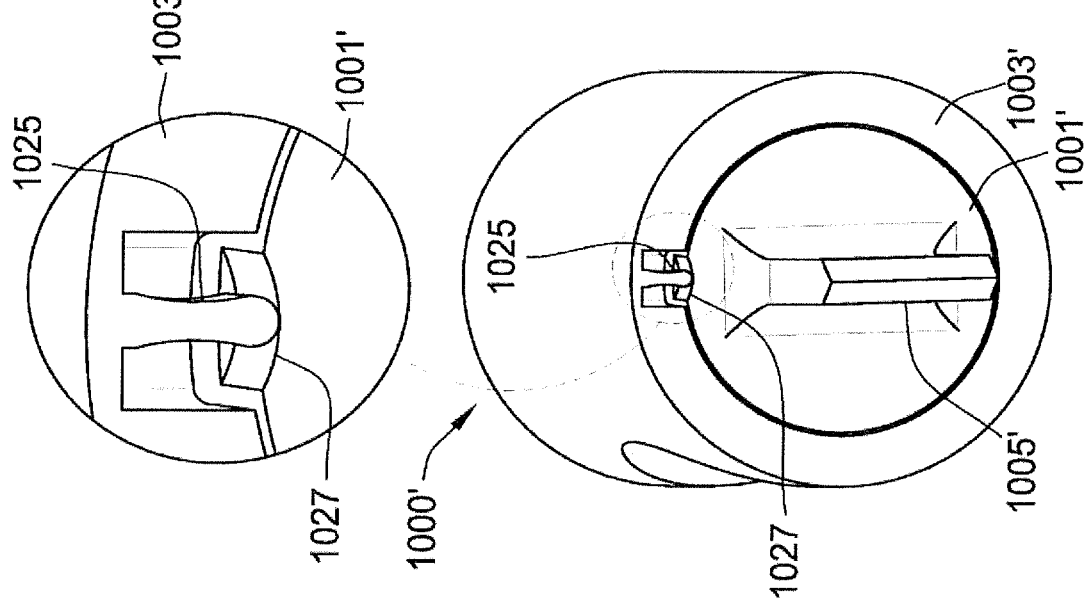

According to some alternative implementations, the flexible arm 1007 (FIGS. 10F and 10G) and the recess 1009 (FIGS. 10F and 10G) can be modified to provide direction-independent resistance to obstruct the inner member 1001 (FIGS. 10F and 10G) from rotating relative to the outer member 1003 (FIGS. 10F and 10G). Specifically, FIGS. 10H and 10I, show a drive hub 1000' that is identical to the drive hub 1000 of FIGS. 10A-10C except that the outer member 1003' of the drive hub 1000' includes a flexible arm 1025 that projects generally perpendicularly towards the surface of the inner member 1001', rather than on an angle as the flexible arm 1007 in FIGS. 10A-10C. Further, the inner member 1001' of the drive hub 1000' includes a recess 1027 that that accepts the end of the flexible arm 1025, rather than the recess 1009 in FIGS. 10A-10C. According to some implementations, the end of the flexible arm 1025 can have a shape that corresponds with the shape of the recess 1027.

With the flexible arm 1025 engaged within the recess 1027, as illustrated in FIG. 10H, the rigidity of the flexible arm 1025 provides resistance to the inner member 1001' rotating relative to the outer member 1003' both in a clockwise direction and in a counterclockwise direction. The resistance obstructs the inner member 1001' from rotating relative to the outer member 1003' prior to the drive hub 1000' being coupled to a hand piece (e.g., hand piece 103).

Once the drive hub 1000' is coupled to a hand piece, the motor of the hand piece can provide sufficient rotational force to overcome the resistance provided by the flexible arm 1025 engaged within the recess 1027 and rotate the inner member 1001' relative to the outer member 1003', as shown in FIG. 10I (e.g., both in a clockwise direction and in a counterclockwise direction). The rotational force disengages the flexible arm 1025 from the recess 1027. Because of the configuration of the flexible arm 1025 and the recess 1027, the hand piece can rotate the inner member 1001' clockwise or counterclockwise relative to the outer member 1003' by applying the sufficient rotational force in either direction.

Accordingly, the flexible arm 1025 and the recess 1027 obstruct the inner member 1001' from rotating relative to the outer member 1003' until the drive hub 1000' engages the hand piece and the hand piece provides the sufficient rotational force. The drive hub 1000' can be assembled with the flexible arm 1025 engaged within the recess 1027 so that, prior to use, a user does not need to manually lock inner member 1001' relative to the outer member 1003' with the opening (e.g., opening 1017') misaligned with the window (e.g., window 1019').

According to some implementations, the resistance provided by the flexible arm 1025 engaged within the recess 1027 may be sufficient to allow a user of the drive hub 1000' to rotate a shaft of the hand piece (e.g., shaft 133). Specifically, the threshold of resistance provided by the flexible arm 1025 engaged within the recess 1027 may be greater than any resistance associated with manually rotating the shaft of the hand piece using the drive coupler 1005' of the drive hub 1000'. Thus, a user can preliminarily engage the drive coupler 1005' with the shaft of the hand piece and rotate the drive hub 1000' to rotate the shaft without the flexible arm 1025 disengaging from the recess 1027; such as during alignment of the drive hub 1000 with the hand piece for engagement. The user can rotate the drive hub 1000' in both directions based on the configuration of the flexible arm 1025 and the recess 1027. Once aligned, the motor of the hand piece can overcome the threshold of resistance provided by the flexible arm 1025 and the recess 1027 to rotate the inner member 1001'.

Although shown in FIGS. 10H and 10I as having a specific shape and arrangement, the flexible arm 1025 and the recess 1027 can have various different shapes and arrangements while still being capable of providing a direction-independent threshold of resistance to obstruct the inner member 1001' from rotating relative to the outer member 1003'. By way of example, and without limitation, the end of the flexible arm 1025 and the recess 1027 may have a square shape, a rectangular shape, a circular shape, an ovular shape, a triangular shape, etc. Further, the shape of the end of the flexible arm 1025 may be different than the shape of the recess 1027, but still configured to engage the recess 1027. For example, the shape of the end of the flexible arm 1025 may be circular and the shape of the recess 1027 may be rectangular.

The depth of the recess 1027 can vary depending on the resistance to be generated by the engagement of the flexible arm 1025 and the recess 1027. Generally, the depth of the recess 1027 and the depth that the flexible arm 1025 engages within the recess are sufficient to rotationally lock the inner member 1001' relative to the outer member 1003' prior to use (e.g., during shipment, transportation, etc. and prior to coupling the drive hub 1001' to the hand piece). By way of example, and without limitation, the depth of the recess can be less than five mm, less than three mm, less than two mm, or less than one mm. However, the depth can vary without departing from the spirit and scope of the present disclosure.

FIGS. 11A and 11B show a front view (FIG. 11A) and a rear view (FIG. 11B) of a surgical device 1100, in accord with additional implementations of the present disclosure. The surgical device 1100 includes features that are similar to the features of the surgical device 10 discussed above with respect to FIGS. 1A-1C. Accordingly, the surgical device 1100 includes a drive housing 1101 that couples to a hand piece 1103. The hand piece 1103 includes a shaft 1105. The hand piece 1103 can optionally include a ring 1107 around the shaft 1105.

The drive housing 1101 includes an inner member 1109 rotatably supported within an outer member 1111 at a proximal end 1101a of the drive housing 1101. The inner member 1109 includes an opening 1113, and the outer member 1111 includes a window 1115, e.g., similar to the arrangement of the inner member 161 and the outer member 163 of the surgical device 10. The inner member 1109 also includes a drive coupler 1117 that couples to the shaft 1105 of the hand piece 1103 when the drive housing 1101 and the hand piece 1103 are coupled. An insert portion 1119 couples to a distal end 1101b of the drive housing 1101 and is inserted into a patient during a procedure using the surgical device.

Rather than the inner member 1109 and the outer member 1111 including the locking elements 201a and 201b and the openings 203a and 203b, respectively, of the surgical device 10, according to some implementations, the outer member 1111 includes a flexure 1121. At one end, the flexure 1121 extends from the outer member 1111 towards the proximal end 1101a of the drive housing 1101. At the other end, the flexure 1121 engages with the inner member 1109 in a first arrangement to rotatably lock the inner member 1109 relative to the outer member 1111 in the first arrangement. The flexure 1121 engages with an element 1123 on an outer diameter of the inner member 1109. The engagement of the flexure 1121 with the element 1123 rotationally locks the inner member 1109 relative to the outer member 1111 in a first arrangement. The element 1123 can be, for example, a ridge, a recess, etc. The element 1123 is positioned on the inner member 1109 such that, when the flexure 1121 engages with the element 1123, the opening 1113 of the inner member 1109 is not aligned with the window 1115 of the outer member 1111 to obstruct the flow of fluid (or fluid and material) from out of (or into) the inner member 1109.

The hand piece 1103 includes a ridge 1125 on an inner diameter of the hand piece 1103. Upon coupling the drive housing 1101 to the hand piece 1103, the ridge 1125 engages the flexure 1121 and causes the flexure 1121 to disengage from the element 1123 on the inner member 1109. Accordingly, the ridge 1125 forces the flexure 1121 into a second arrangement that is disengaged from the element 1123. In the second arrangement, the inner member 1109 is free to rotate relative to the outer member 1111 based on the flexure 1121 disengaging from the element 1123.

The drive housing 1101 includes a latch 1127 (FIG. 11B) that engages a slot 1129 on the hand piece 1103. Engagement of the latch 1127 with the slot 1129 locks the hand piece 1103 to the drive housing 1101 rotationally and longitudinally along the center axis of the surgical device 1100.

The positions of the flexure 1121 and the drive coupler 1117 on the drive housing and the positions of the shaft 1105 and the ridge 1125 on the hand piece 1103 are configured so that the drive coupler 1117 engages the shaft 1105 before the ridge 1125 engages the flexure 1121 when the drive housing 1101 is brought into engagement with the hand piece 1103. Accordingly, the inner member 1109 remains rotationally locked when the drive coupler 1117 engages the shaft 1105, which allows a user to rotate the drive housing 1101 relative to the hand piece 1103 to rotate the shaft 1105 based on rotation of the drive coupler 1117. Further, the latch 1127 is configured to remain in an unlocked position relative to the slot 1129 during rotation of the drive housing 1101 relative to the hand piece 1103 to allow the shaft 1105 and the drive coupler 1117 to engage and align, and the latch 1127 to align with the slot 1129.

Upon the shaft 1105 and the drive coupler 1117 engaging and aligning, and the latch 1127 aligning with the slot 1129, the drive housing 1101 and the hand piece 1103 can be brought into further engagement, which causes the ridge 1125 to engage the flexure 1121 and unlock the inner member 1109 from the outer member 1111. In this unlocked position, the latch 1127 locks with the slot 1129. Accordingly, the hand piece 1103 is configured to drive (e.g., rotate) the inner member 1109 relative to the outer member 1111 to drive the insert portion 1119.

In an embodiment, the drive housing 1101 is initially assembled with the inner member 1109 in the first arrangement with the flexure engaged with the inner member 1109, and the opening 1113 locked in misalignment with the window 1115. By being assembled in the first arrangement, the rotation of the inner member 1101 relative to the outer member 1111 is resisted such that the opening 1113 is obstructed from aligning with the window 1115. Accordingly, the drive housing 1101 is maintained in an arrangement that obstructs aspiration of fluid (or fluid and material) through the inner member 1101 prior to coupling the drive housing 1101 to the hand piece 1103. Coupling the drive housing 1101 to the hand piece 1103 brings the ridge 1125 into engagement with the flexure, which rotationally unlocks the opening 1113 relative to the window 1115 and allows the hand piece 1103 to drive the inner member 1109.

According to the foregoing, the drive housing 1101 can be assembled in the first arrangement such that a user (e.g., doctor, clinician, technician, etc.) of the drive housing 1101 does not need to manually control the position of the opening 1113 relative to the window 1115 prior to using the drive housing 1101, such as prior to coupling the drive housing 1101 to the hand piece 1103, prior to inserting the insert portion 1119 connected to the drive housing 1101 into the patient, after inserting the insert portion 1119 into the patient, or prior to withdrawing the insert portion 1119 from within the patient. Unwanted fluid loss as a result of uncontrolled aspiration of fluid is reduced or prevented because the opening 1113 is initially misaligned with the window 1115 until connecting the drive housing 1101 to the hand piece 1103 and operating the drive housing 1101 to align the window 1115 with the opening 1113.

While the present disclosure has been described with reference to one or more particular implementations, those skilled in the art will recognize that many changes may be made thereto without departing from the spirit and scope of the present disclosure. The above described implementations, and obvious variations thereof, are contemplated as falling within the spirit and scope of the disclosure.

What is claimed is:

1. A surgical device, comprising:
   an end effector assembly including an outer member and an inner member movable within and relative to the outer member, wherein, in a first arrangement of the end effector assembly, the inner and outer members are locked relative to one another to inhibit a relative movement therebetween and, in a second arrangement of the end effector assembly, the inner and outer members are unlocked relative to one another to permit the relative movement therebetween; and
   a handpiece configured to releasably engage the end effector assembly, wherein engagement of the handpiece with the end effector assembly causes relative translation between the inner and outer members to thereby change the end effector assembly from the first arrangement to the second arrangement.

2. The surgical device according to claim 1, wherein the engagement of the handpiece with the end effector assembly causes the inner member to translate relative to the outer member to thereby change the end effector assembly from the first arrangement to the second arrangement.

3. The surgical device according to claim 1, further comprising at least one locking element associated with the end effector assembly, the at least one locking element movable from a locked condition to an unlocked condition to thereby change the end effector assembly from the first arrangement to the second arrangement.

4. The surgical device according to claim 3, wherein the at least one locking element is flexible.

5. The surgical device according to claim 3, wherein the handpiece includes an edge that engages the at least one locking element to move the at least one locking element from the locked condition to the unlocked condition upon engagement of the handpiece with the end effector assembly.

6. The surgical device according to claim 3, wherein at least one recess is defined within the outer member and wherein the at least one locking element engages the at least one recess of the outer member in the first arrangement.

7. The surgical device according to claim 3, wherein the end effector assembly further includes a coupler connected with the inner member, and wherein the at least one locking element extends from the coupler to engage the outer member in the first arrangement.

8. The surgical device according to claim 7, wherein the coupler is configured to engage a drive shaft of the handpiece upon engagement of the handpiece with the end effector assembly.

9. The surgical device according to claim 8, wherein the handpiece further includes a motor configured to drive rotation of the drive shaft.

10. The surgical device according to claim 1, wherein the inner member includes an elongated inner shaft defining an opening and wherein the outer member includes an elongated outer shaft defining a window, and wherein the opening and the window are misaligned relative to one another in the first arrangement of the end effector assembly.

11. The surgical device according to claim 10, wherein the elongated inner shaft includes a cutter in communication with the opening.

12. The surgical device according to claim 1, wherein the relative movement is rotation.

* * * * *